(12) United States Patent
Phillips et al.

(10) Patent No.: US 7,272,445 B2
(45) Date of Patent: Sep. 18, 2007

(54) MEDICAL DEVICE PROGRAMMER WITH FACEPLATE

(75) Inventors: William C. Phillips, Brooklyn Park, MN (US); Mark E. Schommer, Maple Grove, MN (US); John W. Forsberg, St. Paul, MN (US); Alex C. Toy, North St. Paul, MN (US); David P. Olson, Minnetrista, MN (US)

(73) Assignee: Medtronic, Inc., Minneapolis, MN (US)

( * ) Notice: Subject to any disclaimer, the term of this patent is extended or adjusted under 35 U.S.C. 154(b) by 480 days.

(21) Appl. No.: 10/693,006

(22) Filed: Oct. 24, 2003

(65) Prior Publication Data

US 2005/0075686 A1  Apr. 7, 2005

Related U.S. Application Data

(60) Provisional application No. 60/508,511, filed on Oct. 2, 2003.

(51) Int. Cl.
*A61N 1/00* (2006.01)

(52) U.S. Cl. ............... 607/36; 607/59; 607/60; 607/30; 607/31; 607/32; 607/33; 607/34; 607/35; 607/145; 607/156

(58) Field of Classification Search ............... 607/59, 607/60, 5, 43–48, 30–36, 145, 156; 128/897
See application file for complete search history.

(56) References Cited

U.S. PATENT DOCUMENTS

| | | | |
|---|---|---|---|
| 2,144,310 A | 1/1939 | Hyland | |
| 2,147,148 A | 2/1939 | Charrier | |
| 2,203,517 A | 6/1940 | Beggs | |
| 2,273,955 A | 2/1942 | Grimditch | |
| 2,292,182 A | 8/1942 | Van Billiard | |
| 2,343,306 A | 3/1944 | Lear | |
| 2,624,004 A | 12/1952 | Polydoroff | |
| 3,495,264 A | 2/1970 | Spears | |
| 3,683,389 A | 8/1972 | Hollis | |
| 3,796,221 A | 3/1974 | Hagfors | |
| 4,066,086 A | 1/1978 | Alferness et al. | |
| 4,201,965 A | 5/1980 | Onyshkevych | |

(Continued)

FOREIGN PATENT DOCUMENTS

CA   1297206   3/1992

(Continued)

OTHER PUBLICATIONS

Lin et al., "A Wireless PDA-Based Physiological Monitoring System for Patient Transport," IEEE Transactions on Information Technology In Biomedicine, vol. 8, No. 4. p. 439-447; Figure 4 (Aug. 29, 2003).*

(Continued)

*Primary Examiner*—Carl H. Layno
*Assistant Examiner*—Natasha Patel
(74) *Attorney, Agent, or Firm*—Shumaker & Sieffert, P.A.

(57) ABSTRACT

In general, the invention is directed to a patient programmer for an implantable medical device. The patient programmer may include one or more of a variety of features that may enhance performance, support mobility and compactness, or promote patient convenience.

31 Claims, 24 Drawing Sheets

U.S. PATENT DOCUMENTS

| | | | |
|---|---|---|---|
| 4,365,633 A | 12/1982 | Loughman et al. | |
| 4,408,608 A | 10/1983 | Daly et al. | |
| 4,432,360 A | 2/1984 | Mumford et al. | |
| 4,440,173 A | 4/1984 | Hudziak et al. | |
| 4,550,370 A | 10/1985 | Baker | |
| 4,586,508 A | 5/1986 | Batina et al. | |
| 4,601,557 A | 7/1986 | Bogle et al. | |
| 4,690,144 A | 9/1987 | Rise et al. | |
| 4,953,197 A | 8/1990 | Kaewell, Jr. et al. | |
| 5,138,328 A | 8/1992 | Zibrik et al. | |
| 5,302,787 A | 4/1994 | Edds et al. | |
| 5,311,449 A | 5/1994 | Adams | |
| 5,314,457 A | 5/1994 | Jeutter et al. | |
| 5,317,506 A * | 5/1994 | Coutre et al. | 604/65 |
| 5,495,258 A | 2/1996 | Muhlhauser et al. | |
| 5,575,686 A | 11/1996 | Noschese | |
| 5,674,249 A | 10/1997 | de Coriolis et al. | |
| 5,748,103 A | 5/1998 | Flach et al. | |
| 5,807,397 A | 9/1998 | Barreras | |
| 5,833,623 A | 11/1998 | Mann et al. | |
| 5,848,152 A * | 12/1998 | Slipy et al. | 379/433.13 |
| 5,904,708 A | 5/1999 | Goedeke | |
| 5,944,659 A | 8/1999 | Flach et al. | |
| 5,967,986 A | 10/1999 | Cimochowski et al. | |
| 6,073,033 A | 6/2000 | Campo | |
| 6,162,180 A | 12/2000 | Miesel et al. | |
| 6,169,925 B1 | 1/2001 | Villaseca et al. | |
| 6,219,255 B1 | 4/2001 | Teshome | |
| 6,249,703 B1 | 6/2001 | Stanton et al. | |
| 6,263,246 B1 | 7/2001 | Goedeke et al. | |
| 6,308,102 B1 | 10/2001 | Sieracki et al. | |
| D459,814 S | 7/2002 | Lee et al. | |
| 6,415,175 B1 | 7/2002 | Conley et al. | |
| 6,418,346 B1 | 7/2002 | Nelson et al. | |
| 6,426,680 B1 | 7/2002 | Duncan et al. | |
| 6,443,891 B1 | 9/2002 | Grevious | |
| 6,448,933 B1 | 9/2002 | Hill et al. | |
| 6,456,245 B1 | 9/2002 | Crawford | |
| 6,456,887 B1 | 9/2002 | Dudding et al. | |
| 6,469,914 B1 | 10/2002 | Hwang et al. | |
| 6,480,743 B1 | 11/2002 | Kirkpatrick et al. | |
| 6,516,227 B1 | 2/2003 | Meadows et al. | |
| 6,526,310 B1 | 2/2003 | Carter et al. | |
| 6,556,871 B2 | 4/2003 | Schmitt et al. | |
| 6,561,975 B1 | 5/2003 | Pool et al. | |
| 6,567,703 B1 | 5/2003 | Thompson et al. | |
| 6,584,590 B1 | 6/2003 | Bean | |
| 6,614,664 B2 | 9/2003 | Lee | |
| 6,622,031 B1 | 9/2003 | McCleary et al. | |
| 6,622,048 B1 | 9/2003 | Mann et al. | |
| 6,631,296 B1 | 10/2003 | Parramon et al. | |
| 6,636,769 B2 | 10/2003 | Govari et al. | |
| 6,648,821 B2 | 11/2003 | Lebel et al. | |
| 6,654,642 B2 | 11/2003 | North et al. | |
| 6,658,300 B2 | 12/2003 | Govari et al. | |
| 6,678,563 B2 | 1/2004 | Fang et al. | |
| 6,687,538 B1 | 2/2004 | Hrdlika et al. | |
| 6,693,015 B2 | 2/2004 | Carstensen | |
| 6,704,600 B2 | 3/2004 | Daum | |
| 6,731,986 B2 | 5/2004 | Mann | |
| 6,735,474 B1 | 5/2004 | Loeb et al. | |
| 6,754,527 B2 * | 6/2004 | Stroebel et al. | 607/5 |
| 6,804,558 B2 * | 10/2004 | Haller et al. | 607/30 |
| 6,898,283 B2 * | 5/2005 | Wycherley et al. | 379/433.11 |
| 6,930,602 B2 | 8/2005 | Dougherty et al. | |
| 2001/0039437 A1 | 11/2001 | Taepke, II et al. | |
| 2002/0002326 A1 | 1/2002 | Causey et al. | |
| 2002/0052539 A1 | 5/2002 | Haller et al. | |
| 2002/0055761 A1 | 5/2002 | Mann et al. | |
| 2002/0072785 A1 | 6/2002 | Nelson et al. | |
| 2002/0074975 A1 | 6/2002 | Culpepper et al. | |
| 2002/0123673 A1 | 9/2002 | Webb et al. | |
| 2003/0036783 A1 | 2/2003 | Bauhahn et al. | |
| 2003/0050535 A1 | 3/2003 | Bowman, IV et al. | |
| 2003/0050676 A1 | 3/2003 | Hubelbank et al. | |
| 2003/0065308 A1 | 4/2003 | Lebel et al. | |
| 2003/0114899 A1 | 6/2003 | Woods et al. | |
| 2003/0136418 A1 | 7/2003 | Behm | |
| 2003/0139782 A1 * | 7/2003 | Duncan et al. | 607/48 |
| 2003/0161093 A1 | 8/2003 | Lam et al. | |
| 2003/0171789 A1 | 9/2003 | Malek et al. | |
| 2003/0174066 A1 | 9/2003 | Goetz et al. | |
| 2003/0174069 A1 | 9/2003 | Goetz et al. | |
| 2003/0176906 A1 | 9/2003 | Lee | |
| 2003/0177031 A1 | 9/2003 | Malek | |
| 2003/0204233 A1 | 10/2003 | Leinders et al. | |
| 2003/0229383 A1 | 12/2003 | Whitehurst et al. | |
| 2004/0001432 A1 | 1/2004 | Wescott | |
| 2004/0059395 A1 | 3/2004 | North et al. | |
| 2004/0064166 A1 | 4/2004 | Thompson et al. | |
| 2004/0098068 A1 | 5/2004 | Carbunaru et al. | |
| 2004/0100412 A1 | 5/2004 | Kurjenheimo et al. | |
| 2004/0100450 A1 | 5/2004 | Choi | |
| 2004/0106860 A1 | 6/2004 | Say et al. | |
| 2004/0106967 A1 | 6/2004 | Von Arx et al. | |
| 2004/0125016 A1 | 7/2004 | Atwood et al. | |
| 2004/0125029 A1 | 7/2004 | Maoz et al. | |
| 2004/0152953 A1 | 8/2004 | Goedeke | |
| 2004/0199212 A1 | 10/2004 | Fischell et al. | |
| 2004/0230246 A1 * | 11/2004 | Stein et al. | 607/32 |
| 2004/0230247 A1 | 11/2004 | Stein et al. | |
| 2005/0040992 A1 | 2/2005 | Chirila | |
| 2005/0060011 A1 | 3/2005 | Denker et al. | |
| 2005/0075684 A1 | 4/2005 | Phillips et al. | |
| 2005/0075685 A1 | 4/2005 | Forsberg et al. | |
| 2005/0075687 A1 | 4/2005 | Phillips et al. | |
| 2005/0075688 A1 | 4/2005 | Toy et al. | |
| 2005/0075689 A1 | 4/2005 | Toy et al. | |
| 2005/0075690 A1 | 4/2005 | Toy et al. | |
| 2005/0075691 A1 | 4/2005 | Phillips et al. | |
| 2005/0075692 A1 | 4/2005 | Schommer et al. | |

FOREIGN PATENT DOCUMENTS

| | | |
|---|---|---|
| DE | 203 10 991 U1 | 1/2004 |
| EP | 0 806 222 A2 | 11/1997 |
| EP | 1 134 003 A2 | 9/2001 |
| JP | 2000 322244 | 11/2000 |
| WO | WO 02/057994 | 7/2002 |
| WO | WO 03/008014 | 1/2003 |
| WO | WO 03/037430 | 5/2003 |
| WO | WO 03/040986 | 5/2003 |

OTHER PUBLICATIONS

Notification of Transmittal of the International Preliminary Report on Patentability dated Apr. 11, 2005, International Application No. PCT/US2004/002452.

Advanced Neuromodulation Systems New Rapid Programmer, 2003.

ANS' New Palm-Sized Programmer Provides Quick, Convenient Management of Pain Therapy, 2003.

Notification of Transmittal of the International Search Report and the Written Opinion of the International Searching Authority, or the Declaration for International Application No. PCT/US2004/002452, filed Jan. 28, 2004.

Crawford et al., "High-Frequency Microinductors with Amorphous Magnetic Ground Planes," IEEE Transactions of Magnetics, vol. 38, No. 5, pp. 3168-3170, 2002.

"Copper/Polyester Laminate as an EMI/ESD Shield," IBM Technical Disclosure Bulletin, vol. 28, No. 10, pp. 4342-4343, 1986.

* cited by examiner

MEDICAL DEVICE PROGRAMMER WITH FACEPLATE

This application claims priority from U.S. provisional application Ser. No. 60/508,511, filed Oct. 2, 2003, the entire content of which is incorporated herein by reference.

TECHNICAL FIELD

The invention relates to medical devices and, more particularly, to handheld programmers for medical devices.

BACKGROUND

Medical devices are used to deliver therapy to patients to treat a variety of symptoms or conditions, and may be implantable or external. An implantable neurostimulator, for example, may treat symptoms or conditions such as chronic pain, tremor, Parkinson's disease, epilepsy, incontinence, or gastroparesis. The implantable medical device delivers neurostimulation therapy via one or more leads that include electrodes located proximate to the spinal cord, pelvic nerves, or stomach, or within the brain of a patient. In general, the implantable medical device delivers neurostimulation therapy in the form of electrical pulses.

A clinician selects values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. In addition, the clinician also selects particular electrodes within an electrode set to be used to deliver the pulses, and the polarities of the selected electrodes.

The clinician uses a clinician programmer to program the parameters into the implantable medical device. The implantable medical device may store multiple programs, however, which may be selected by the patient using a patient programmer. The patient may select different programs to modify therapy delivered by the implantable medical devices, e.g., to achieve greater pain relief. Different programs may be appropriate for different times of day or different physical activities or postures.

The patient programmer communicates with the implantable medical device to modify programs using radio frequency (RF) telemetry. For this reason, the patient programmer includes an external antenna with an RF telemetry head for placement on the patient's body at a position near the implantable medical device. The patient programmer is typically designed as a mobile device that may be carried by the patient throughout the course of the day. For example, the patient programmer may be a handheld device, and typically is powered by batteries within the device.

SUMMARY

In general, the invention is directed to a handheld programmer, such as a patient programmer, for a medical device. The medical device may be an implantable medical device, an external medical device, or a medical device with external and implanted components. The handheld programmer will be described in conjunction with an implantable neurostimulator for purposes of illustration. The patient programmer may include one or more of a variety of features that may enhance performance, support mobility and compactness, or promote patient convenience.

For example, a patient programmer in accordance with an embodiment of the invention may include both an internal antenna for RF telemetry with an implantable medical device and a display device. An external antenna also may be attached to the patient programmer via a cable, and may include an RF telemetry head for placement on the patient's body at a position near an implanted medical device.

The small nature of the handheld patient programmer makes it desirable to locate the display, internal antenna, batteries and printed circuits board in very close proximity to each other. However, when any of these components are located near each other, poor RF communication can result from a number of electronic issues such as: noise injection, noise coupling, and unwanted antenna loading. The invention described herein, in some embodiments, addresses these issues and results in a small handheld device with superior and reliable RF communication.

The internal antenna is mounted within the patient programmer housing, and may have a structure designed for performance and compactness. In addition, the internal antenna may facilitate programming of the implanted medical device by simply placing the patient programmer on the patient's body at a position near the implanted medical device, thereby promoting patient convenience.

In addition, the internal antenna may have a loop-like structure that defines a central aperture. The central aperture may be shaped and sized to accommodate insertion of one or more batteries into the programmer. In some embodiments, the loop-like structure may be substantially rectangular. The batteries may be mounted in a battery bay within the antenna aperture. In some embodiments, the battery bay protrudes into the antenna aperture from the patient programmer housing.

The batteries may be placed in the battery bay via an access door on the outside of the patient programmer housing. In some cases, the batteries may contribute favorably to the RF load presented to the internal antenna. In particular, the batteries may present an additional load to the internal antenna, enhancing immunity to electrical and electromagnetic interference during telemetry sessions with the implantable medical device. To further reduce electrical and electromagnetic interference, the internal antenna may be constructed with a woven copper braid that enhances shielding and reduces antenna loading during transmission and reception.

The display in the patient programmer may include a display screen, such as a liquid crystal display (LCD), to present status information and other messages to the patient. To reduce the effects of electrical and electromagnetic interference produced by the display screen, and associated display electronics, on telemetry performance, the display screen and internal antenna may be displaced from one another within the patient programmer housing.

For example, the antenna and associated transmit and receive electronics may be mounted on a first circuit board, and the display and associated display electronics may be mounted on a second circuit board. The first and second circuit board may occupy different planes, displaced from one another, within the patient programmer housing. However, the display and antenna may overlap one another, providing a compact, stack-like configuration.

The internal antenna may be mounted on an outward-facing side of the first circuit board, and the display may be mounted on an outward-facing side of the second circuit board. In some embodiments, the internal antenna may be mounted to a bottom housing cover above the surface of the first circuit board, and electrically connected to the circuit board via a connector. In this manner, the internal antenna also may be displaced from the first circuit board.

The separation distance between the circuit boards may serve to reduce the effects of electrical and electromagnetic interference caused by the display on signals transmitted and received by the internal antenna. In addition, the placement of the antenna and display electronics on different circuit boards may reduce electrical and electromagnetic interference. In summary, the internal antenna arrangement provides a compact design, but reduces the effects of circuit board noise on telemetry performance.

In some embodiments, a majority of digital electronics may be placed on the first circuit board with the display, and a majority of analog and RF electronics may be placed on the second circuit board. Consequently, much of the digital electronics on one circuit board may be selectively turned off during telemetry sessions administered by analog components on the other circuit board. In this manner, the programmer can be configured to reduce the impact of significant electrical and electromagnetic noise on telemetry performance.

For example, the patient programmer may include a processor or other control circuitry that selectively disables, i.e., turns off, the display during RF telemetry with the internal antenna to promote more reliable communication. The processor or control circuitry also may disable electronics associated with the display during a telemetry session. For example, the display and display electronics may be temporarily disabled during reception of RF signals from the IMD, transmission of RF signals to the IMD, or both.

In this manner, the patient programmer selectively controls the display and display electronics to reduce electrical and electromagnetic interference. The processor enables the display and display electronics upon completion of telemetry. When use of an external antenna is detected, the processor may enable the display, as electrical and electromagnetic interference may be less of a concern for the external antenna, which extends away from the patient programmer via a cable, e.g., by several inches or feet.

The patient programmer also may feature a stacked configuration that permits Z-axis assembly of the components of the programmer, including a bottom housing cover, the antenna, the antenna circuit board, the display circuit board, a display lens cover faceplate that protects the display, input buttons, and the top housing cover. In this manner, the various components may be stacked on top of one another to build the patient programmer from back to front.

The display lens cover faceplate may be an in-mold decorated lens faceplate that can be printed with distinctive indicia just prior to assembly to customize the appearance of the programmer, and then inserted into the front housing cover, e.g., within a recessed area or opening in the front housing cover. In some cases, the display lens cover faceplate may be printed with personalization information, such as patient name, address and phone number.

Also, the display lens cover faceplate may carry different graphics to distinguish different types of therapy delivered by the medical device, or distinguish different model types. The faceplate also may be made with different configurations that expose different sets of buttons, and may have different appearances, including different colors, illustrations, and designs, while fitting in a common mounting area. Such features, including particularly different sets of buttons, may be appropriate to particular types or models of medical devices.

An external antenna used with the patient programmer may include a cable and a loop-like telemetry head at one end of the cable. The loop-like telemetry head is placed on the patient's body at a position near the implanted medical device. The loop-like telemetry-head may define a unique aperture with a wide end and a narrow, tapered end, e.g., somewhat similar to the shape of a tear drop. The narrow, tapered end of the aperture defines a channel or "notch" designed to capture clothing worn by the patient to thereby hold the telemetry head in place near the implanted medical device during programming. When the clothing, such as a shirt, is forced into the channel, an interference fit or friction tends to hold the clothing and the telemetry head in place relative to one another.

In some embodiments, the patient programmer may be programmed via a software loading port, such as a JTAG interface. In particular, the programmer may include non-volatile memory, such as flash memory or CPLDs that may be programmed with basic operating system functionality and programs via a software loading port during initial assembly. The software loading port may be exposed via the front housing cover, e.g., prior to place of the lens cover faceplate. For example, the front housing cover may present an aperture that permits access to the software loading port, but is covered by the lens cover faceplate when it is placed in the front cover housing. In this manner, the programmer may be programmed as one of the final steps in the manufacturing process.

This feature enables a large number of programmers to be preassembled, placed in storage if desired, and then programmed for operation with an appropriate type of medical device, e.g., just before the lens cover faceplate is placed in the front housing cover. A programming head may be sized and shaped to engage the software loading interface and download software from a host computer such as a handheld computing device. Hence, large numbers of programmers can be stockpiled, and then loaded with appropriate operating system and application software to specially configure the programmer with one of a plurality of functional sets for use with a specific type of programmer and IMD.

Following assembly, the patient programmer may be reprogrammed, updated or upgraded via an infrared interface provided in the patient programmer. Unlike the software loading port, which may be covered by the lens cover faceplate upon assembly, the infrared interface is exposed for interaction with an infrared communication device. For example, the infrared interface may be activated when the device is powered up, e.g., by activating an "on" button on the patient programmer or replacing batteries in the programmer. Upon power-up, the infrared interface enters a programming state, i.e., a listening period, in which it is capable of establishing an infrared communication session for field updates and upgrades to the embedded operating system.

For example, the infrared interface may remain active for initiation of a communication session for a period of time following power-up, i.e., a finite listening period. A dedicated programming device or a clinician programmer may include an infrared interface to communicate with the infrared interface of the patient programmer, and provide updates to software or firmware. In this manner, the embedded operating system and, in some cases, medical device programs in the patient programmer may be updated in the field. If no external infrared communication device is detected within a period of time, e.g., seconds, following power-up, the infrared interface may go inactive. The infrared interface for updates and upgrades in the field may be provided in addition to a software loading interface that is used to initially load the operating system software and application software upon manufacture and assembly of the programmer.

In accordance with another embodiment, a circuit board within the programmer, e.g., a circuit board on which an internal antenna is mounted or placed nearby, may be configured to further promote telemetry performance. For example, a ground plane may be provided with a substantially continuous ground plane area interrupted by a plurality of gaps that extend generally outward from a center of the circuit board. A single, contiguous ground plane area is desirable to provide a low impedance return path for electrical signals transmitted via traces on signal planes. The gaps define sub-areas, which may be dedicated to providing low impedance return paths to maintain signal integrity for respective signal groups on the signal planes.

In addition, the signal planes in the antenna circuit board may be configured to present a reduced magnetic load to the magnetic circuit operating on the antenna. Reduction or elimination of surface area of the conductive signal planes within the antenna aperture serves to reduce the magnetic load to the magnetic circuit of antenna. In particular, the signal planes may include electrostatic discharge layers that define apertures in alignment with, and sized and shaped similarly to, the aperture of antenna to substantially reduce the magnetic load.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
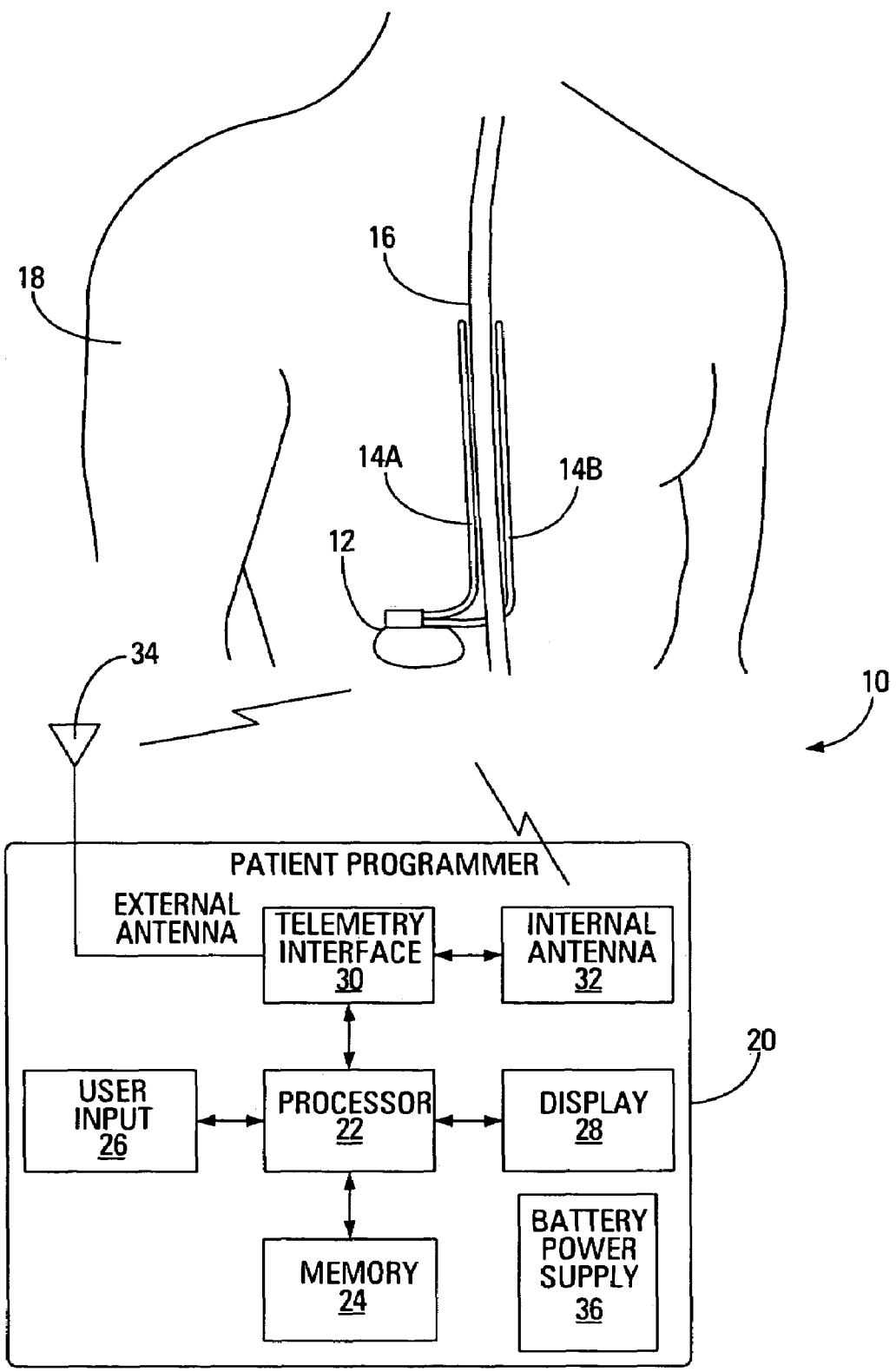
FIG. 1 is a conceptual diagram illustrating a system for programming and delivering medical therapy.

FIG. 1 is a conceptual diagram illustrating a system 10 for programming and delivering medical therapy to a patient 18. In the example of FIG. 1, system 10 includes an implantable medical device 12, in the form of an implanted neurostimulator, that delivers neurostimulation therapy to patient 18. Hence, IMD 12 may be an implantable pulse generator, and may deliver neurostimulation therapy to patient 18 in the form of electrical pulses. In some embodiments, IMD 12 may include a rechargeable battery power supply that can be transcutaneously recharged periodically to maintain operating power within the IMD. System 10 may incorporate one or more of a variety of features designed to enhance performance, support mobility and compactness, or promote patient convenience.

IMD 12 delivers neurostimulation therapy to patient 18 via leads 14A and 14B (collectively "leads 14"). Leads 14 may, as shown in FIG. 1, be implanted proximate to the spinal cord 16 of patient 18, and IMD 12 may deliver spinal cord stimulation (SCS) therapy to patient 18 in order to, for example, reduce pain experienced by patient 18. However, the invention is not limited to the configuration of leads 14 shown in FIG. 1 or the delivery of SCS therapy. For example, one or more leads 14 may extend from IMD 12 to the brain (not shown) of patient 18, and IMD 12 may deliver deep brain stimulation (DBS) therapy to patient 18 to, for example, treat tremor or epilepsy. As further examples, one or more leads 14 may be implanted proximate to the pelvic nerves (not shown) or stomach (not shown), and IMD 12 may deliver neurostimulation therapy to treat incontinence or gastroparesis.

IMD 12 delivers neurostimulation therapy to patient 18 according to one or more neurostimulation therapy programs. A neurostimulation therapy program may include values for a number of parameters, and the parameter values define the neurostimulation therapy delivered according to that program. In embodiments where IMD 12 delivers neurostimulation therapy in the form of electrical pulses, the parameters may include pulse voltage or current amplitudes, pulse widths, pulse rates, and the like. Further, each of leads 14 includes electrodes (not shown), and the parameters for a program may include information identifying which electrodes have been selected for delivery of pulses according to the program, and the polarities of the selected electrodes.

System 10 also includes a patient programmer 20. Programmer 20 may be a handheld computing device. Ideally, the handheld patient programmer 20 should be small enough to be concealed discreetly by the patient and still result in reliable RF communication with IMD 12. Patient programmer 20 includes a processor 22 that executes instructions stored in memory 24 to control functions performed by the patient programmer. Processor 22 may include a microprocessor, a controller, a DSP, an ASIC, an FPGA, discrete logic circuitry, or the like.

Patient programmer 20 further includes a display 28, such as a LCD, LED or plasma display, to display information to a user. Programmer 20 may also include a user input device 26, which may be used by a user to interact with programmer 20. In some embodiments, display 28 may be a touch screen display, and a user may interact with programmer 20 via display 28. A user may also interact with programmer 20 using peripheral pointing devices, such as a stylus or mouse. User input device 26 may take the form of an alphanumeric keypad or a reduced set of keys associated with particular functions.

Processor 22 drives display electronics associated with display 28 to present status information and other data to patient 18. Advantageously, display 28 may provide graphical information, textual information, or both to indicate the status of operation of programmer 20 and IMD 12. Consequently, when changing programs, device settings (such as neurostimulation parameter settings, or other features, patient 18 may receive visual feedback directly from programmer 20 as to the status of the changes. Thus, in the context of neurostimulation, for example, patient 18 need not rely merely on changes in sensation (e.g., paresthesia) or audible beeps indicating the progress of changes to assess whether the changes have been made. Visual presentation on display 28 may be provided in conjunction with audible tones, beeps, or even audible voice advisories.

Also, programmer 20 may interact with IMD 12 to assess operation and status of the IMD 12. For example, programmer 20 may interrogate IMD 12 to ascertain the charge status of a rechargeable battery power supply within IMD 12. In this manner, programmer 20 may advise patient 18 of the current charge status, and indicate when recharge is necessary or advisable. The charge status may be presented to patient 18 on display 28 as a percentage, number, bar representation, or other graphical, textual or iconic representation that conveys to the patient the battery charge status within IMD 12. Of course, display 28 may also convey the battery charge status for batteries within programmer 20 itself, in a similar manner to the presentation of battery charge for IMD 12.

Further, in some embodiments, display 28 may provide the opportunity to present graphical depictions of the status of IMD 12, including the status of leads and electrodes and portions of the body targeted for therapy by those leads and electrodes. Also, when an external antenna is used for telemetry with IMD 12, display 28 may present an indication of the location of the antenna relative to the IMD 12 for a telemetry session, e.g., based on telemetry signal strength between the antenna and IMD 12.

In addition, processor 22 receives user input entered by a user via user input 26 to control various operations performed by patient programmer 20. Processor 22 also controls a telemetry interface 30 to transmit and receive information, such as instructions and status information. In particular, telemetry interface 30 drives one or both of an internal antenna 32 and an external antenna 34 to transmit instructions to IMD 12. In addition, telemetry interface 30 processes signals received by internal antenna 32 and external antenna 34 from IMD 12. Internal antenna 32 is mounted within a housing associated with patient programmer 20, whereas external antenna 34 extends outward from patient programmer 20 via an antenna cable. Notably, as shown in FIG. 1, programmer 20 may include both a display 28 and internal antenna 32.

Patient 18 carries programmer 20 and uses the programmer to program neurostimulation therapy for the patient throughout the course of the patient's day. Again, however, certain aspects of the invention are not limited to patient programmers, but also may contemplate clinician programmers. For a neurostimulation application, if IMD 12 is appropriately configured, programmer 20 may control IMD 12 to support delivery of multiple programs simultaneously, in an interleaved manner. For example, two or more programs may be delivered on an interleaved basis. This is beneficial because it affords the physician more flexibility when attempting to cover a patient's pain area with paresthesia. Additional programs give the physician more options to optimize the pain area with paresthesia, when needed.

In the interest of portability, patient programmer 20 further includes a battery power supply 36, as mentioned above. Patient 18 may use programmer 20 to select different programs or modify parameter settings, such as amplitude, rate, electrode configuration, and the like to enhance therapeutic effects. Program or parameter changes may be appropriate for changes in physical activities, postures, time of day, or other events. Different programs or parameters may have different results in terms of symptom relief, coverage area relative to symptom area, and side effects.

A clinician programmer (not shown) may be used by a clinician to create neurostimulation therapy programs and load the programs either into memory associated with IMD 12 or patient programmer 20. Hence, in some embodiments, patient programmer 20 may be configured to download programs stored in memory associated with the patient programmer to IMD 12 to initiate new programs or modify existing programs. In other embodiments, however, patient programmer 20 merely communicates instructions to IMD 12 to select different programs or parameters settings from memory in the IMD. Memory 24 of patient programmer 20 may include a nonvolatile form of read-only memory (ROM), such as flash memory, EEPROM, FPGA, CPLD, or the like, and may store application software for execution of instructions by processor 22, device parameters, use data, diagnostic data, and other software related information. Read-only memory contents are retained without application of power. Alternatively, or in addition, memory 24 may include random access memory (RAM).

In order to modify programs and parameter settings and otherwise control IMD 12, patient programmer 20 communicates with IMD 12 via wireless telemetry techniques. For example, programmer 20 may communicate with IMD 12 via RF telemetry. In this manner, patient programmer 20 is used by patient 18 to control the delivery of neurostimulation therapy by IMD 12. For telemetry with IMD 12, patient programmer 20 may use either internal antenna 32 or external antenna 34 on a selective basis.

External antenna 34 may be attached to the patient programmer 20 via a cable, and many include an RF telemetry head for placement on the patient's body at a position near IMD 12. Internal antenna 32 is mounted within or on the housing of patient programmer 20, and may have a structure designed for performance and compactness. In addition, internal antenna 32 may facilitate programming of the IMD 12 by simply placing the patient programmer 20 on the patient's body at a position near the implanted medical device, thereby promoting patient convenience.

Display 28 and associated display electronic can produce significant electrical and electromagnetic interference capable of degrading the performance of internal antenna 32 during telemetry sessions. This interference may be particularly troublesome due to the relatively close proximity of internal antenna 32 to display 28 within the housing of patient programmer 20. For this reason, processor 22 or other control circuitry within patient programmer 20 may be configured to selectively disable, i.e., turn off, display 28 and associated display electronics during RF telemetry with internal antenna 32 to promote more reliable communication. For example, display 28 and display electronics may be temporarily disabled during reception of RF signals, transmission of RF signals, or both, by internal antenna 32.

In this manner, patient programmer 20 selectively controls the display 28 and display electronics to reduce electrical and electromagnetic interference. Processor 22 then enables the display 28 and display electronics upon completion of telemetry using internal antenna 32. In some embodiments, patient programmer 20 may control display 28 to display information at a lower intensity, rather than turning off the display. When use of an external antenna 34 is detected, processor 22 may enable display 28, as interference may be less of a concern for the external antenna, which extends away from patient programmer 20 via a cable.

Figure 2:
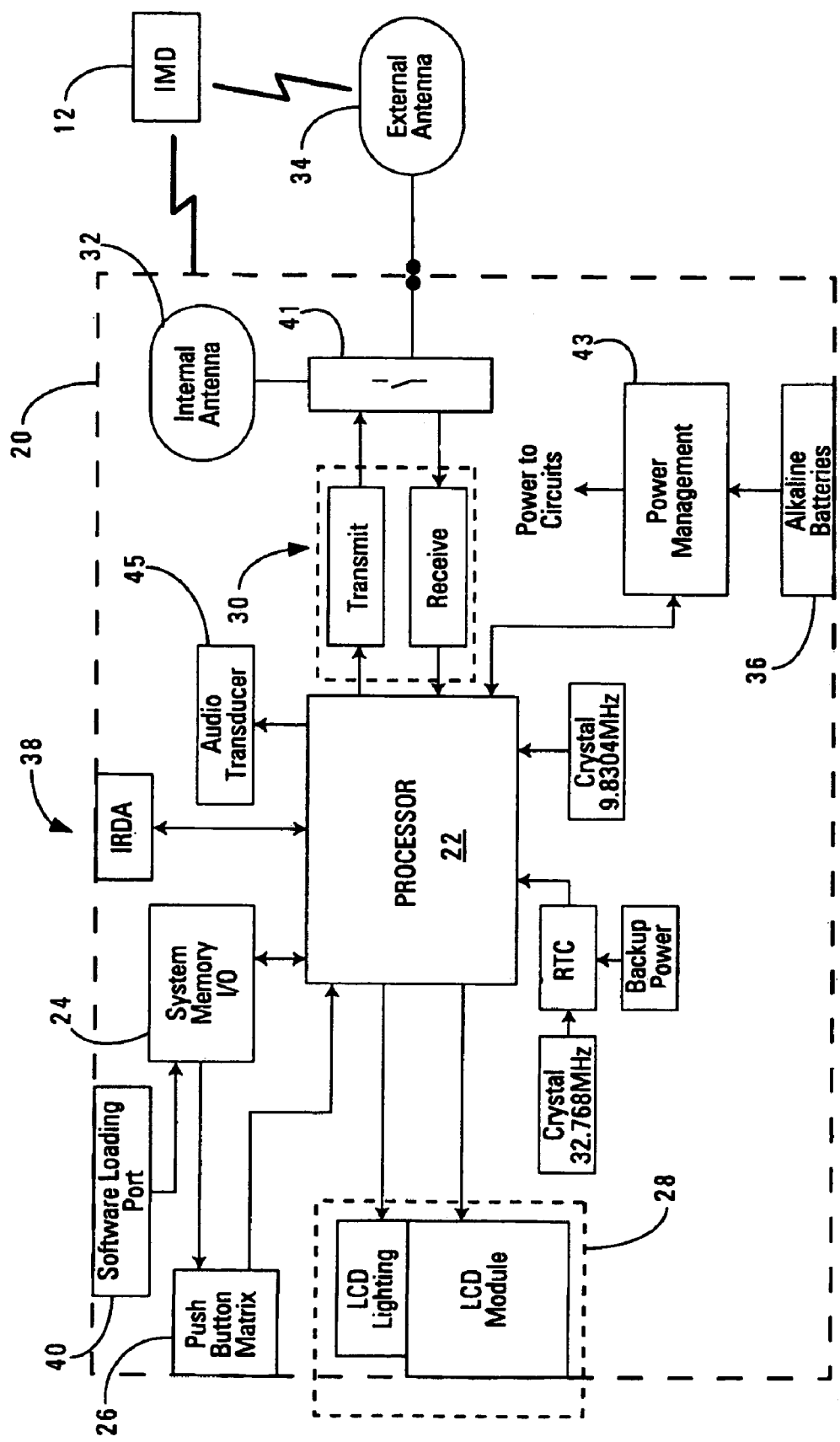
FIG. 2 is a block diagram illustrating a patient programmer for programming an implantable medical device.

FIG. 2 is a block diagram illustrating patient programmer 20 in greater detail. As shown in FIG. 2, display 28 may include an LCD module with an LCD lighting source. In other embodiments display 28 may comprise a plasma display, or the like, that is capable of presenting an icon driven graphical user interface (GUI). However, in this disclosure, the term display is not meant to include indicator LEDs or other non-graphical signals. Also, user input device 26 may include a push button matrix. The push button matrix 26 corresponds to a matrix of input buttons used by patient 18 to alter stimulation parameters and maneuver through the GUI presented by display 28.

An infrared (e.g., IRDA) interface 38 may be provided for upgrades, updates, and reprogramming of the embedded operating system of patient programmer 20 in the field or clinic. The infrared interface 38 may also include a controller (not shown) to control IRDA interface 38 to initiate an infrared communication session for a period of time following power-up of programmer 20. A software loading port 40, such as a Joint Test Action Group (JTAG) interface, conforming to IEEE 1149.1 boundary-scan standard, may be provided, in addition to infrared interface 38, to initially load the embedded operating system into patient programmer 20 and, in particular, into a system memory 24.

Loading interface 40 may be accessible after substantial manufacture of programmer 20 to allow generic programmers to be assembled and later programmed to fill orders. Loading interface 40 may be generally inaccessible after substantial manufacture of programmer 20, e.g., after access to loading interface 40 is blocked by completion of the housing of the programmer 20. Infrared interface 38 may be accessible after complete manufacture of programmer 20, and exposed by the housing of the programmer.

The infrared interface 38 for updates and upgrades in the field may be provided in addition to a software loading interface 40 that is used to initially load the operating system software and application software upon manufacture and assembly of the programmer. In some embodiments, infrared interface 38 may be alternatively realized by different types of communication devices, such as an RF communication device that communicates according to wireless communication technologies such as IEEE 802.11a, 802.11b, 802.11 g, or Bluetooth. In this case, a similar listening period may be provided upon power-up to permit communication with a field programmer.

Telemetry interface 30 includes transmit and receive circuitry, and may be selectively coupled to internal antenna 32 or external antenna 34 via a switch 41. Programmer 20 may include further circuitry to detect external antenna 34, and drive display 28 and telemetry interface 30 based on the detection. Battery power supply 36, in some embodiments, may include one or more alkaline batteries, e.g., AA or AAA batteries, that may be replaced when they are depleted via a door or other access opening in the housing of patient programmer 20. In some cases, the batteries may be rechargeable. The batteries may be placed proximate internal antenna 32 and provide a load to enhance noise immunity to external magnetic interference. A power management circuit 43 delivers power from battery power supply 36 to various components of patient programmer 20. An audio transducer 45 may be provided to emit audible beeps or tones in response to button or keypad entries by the patient 18, or other events.

Figure 3:
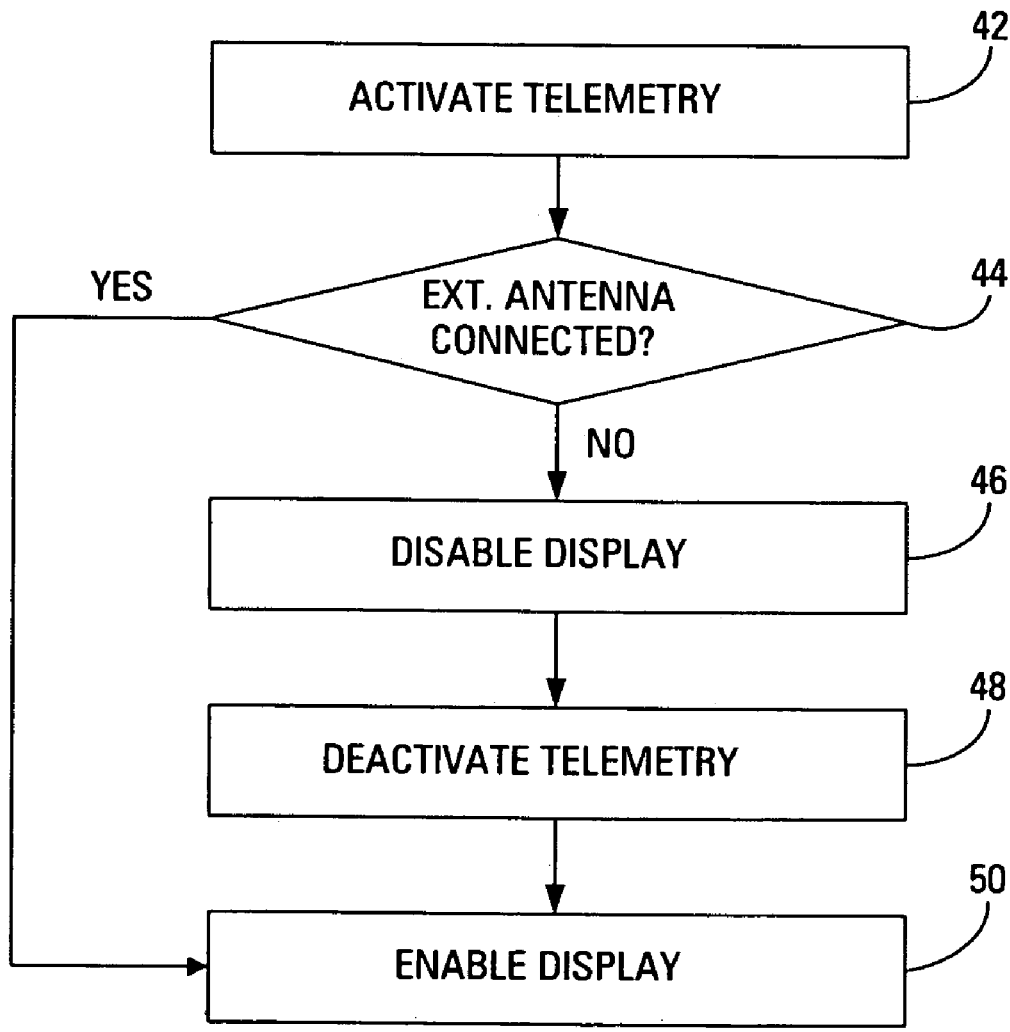
FIG. 3 is a flow diagram illustrating a technique for selectively enabling and disabling a display to reduce electrical and electromagnetic interference during telemetry.

FIG. 3 is a flow diagram illustrating a technique for selectively enabling and disabling display 28 and associated display electronics to reduce electrical and electromagnetic interference during telemetry sessions using internal antenna 32. As shown in FIG. 3, the technique involves activating telemetry interface 30 (42) within patient programmer 20 to initiate a communication session with IMD 12. If the external antenna 34 is connected (44) to the patient programmer 20, display 28 is enabled by processor 22 so that patient 18 can view the display during the telemetry session, if desired. Telemetry integrity of external antenna 34 is not compromised by display 28 due to the length of the cable used to couple external antenna 34 to programmer 20.

If external antenna 34 is not connected (44), or in some embodiments if patient 18 has designated that external antenna will not be used, processor 22 disables display 28 (46) to reduce potential electrical and electromagnetic interference caused by the display and associated display electronics. Space constraints within programmer 20 cause telemetry via internal antenna 32 to be disrupted by display 28. In some embodiments, processor 22 may disable various electronics on an entire circuit board on which display 28 is mounted.

In either case, disabling display 28 reduces electrical and electromagnetic interference, thereby avoiding degradation of telemetry performance when internal antenna 32 is used. Upon deactivating telemetry interface 30 (48), i.e., at the end of or during a pause in the telemetry session with IMD 12, processor 22 enables display 28 so that the display can present information to the user (50). In some embodiments, processor 22 also may selectively disable audio transducer 45 during telemetry to avoid any electrical and electromagnetic interference that may be caused by operation of the audio transducer.

Figure 4:
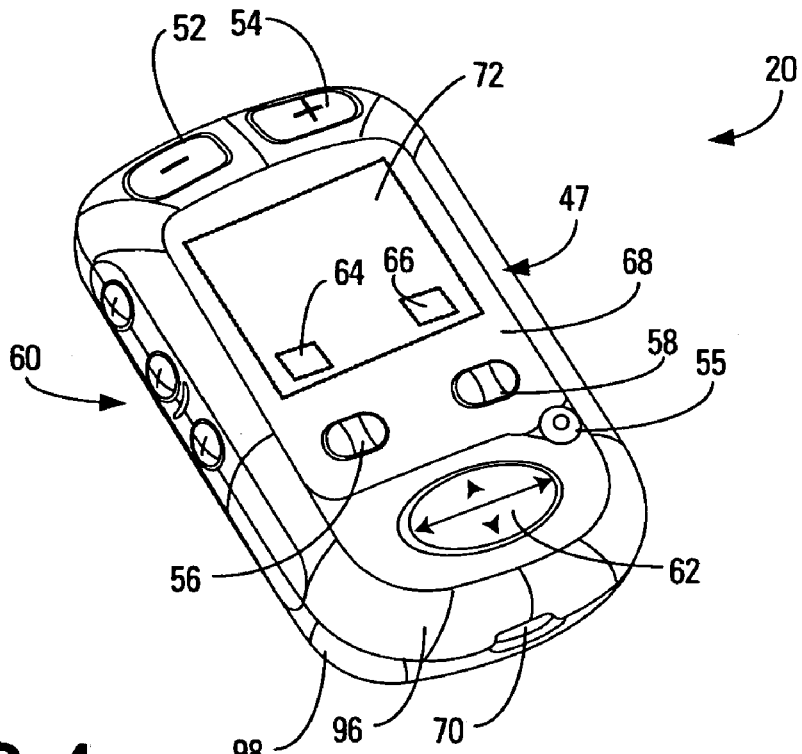
FIG. 4 is a perspective view of a patient programmer.

FIG. 4 is a perspective view of patient programmer 20. As shown in FIG. 4, patient programmer 20 includes a housing 47. Housing 47 may have a height of approximately 8 to 10 cm, a width of approximately 5 to 6 cm, and a thickness of approximately 2 to 3 cm. Housing 47 may be formed of molded plastic and may include a front housing cover 96 and a bottom housing cover 98, as well a lens cover faceplate 68 with a transparent display section 72. Faceplate 68 may be formed of a clear plastic material. Front cover 96 includes a number of input buttons 52, 54, 55, 56, 58, 60, 62. More specifically, front cover 96 may include apertures that permit buttons 52, 54, 55, 56, 58, 60, 62 to protrude through the front cover from the interior of housing 47. Front cover 96 also includes an infrared interface window 70 that exposes an infrared (e.g., IRDA) transmitter and receiver.

Buttons 52, 54 are minus and plus buttons, respectively, that may permit patient 18 to decrease and increase values of neurostimulation parameter settings. In particular, buttons 52, 54 may permit patient 18 to quickly increase and decrease the amplitude of stimulation being delivered by IMD 12. Button 55 is an on/off button that turns power on and off, and turns backlighting on and off. Button 62 is a four-way (up, down, left, right) rocker switch that permits navigation through items presented on display 28.

Buttons 60 may be devoted to a variety of functions such as activation of stimulation, deactivation of stimulation, and interrogation of IMD 12 to check device status. The device status may include remaining battery power and current stimulation parameter settings, and may be displayed on display 28. Buttons 56, 58 correspond to software-defined soft keys 64, 66, respectively, which are presented by display 28. The displayed soft keys 64, 66 may be flexibly reprogrammed to accommodate different functions, features, treatments and contexts. Each button 56, 58, upon depression, specifies user input with respect to the soft keys 64, 66. Any of buttons 52, 54, 55, 56, 58, 60, 62 may have different tactile surfaces or sensations, e.g., different pressures, when pushed to permit the patient to more readily differentiate the buttons.

Figure 5:
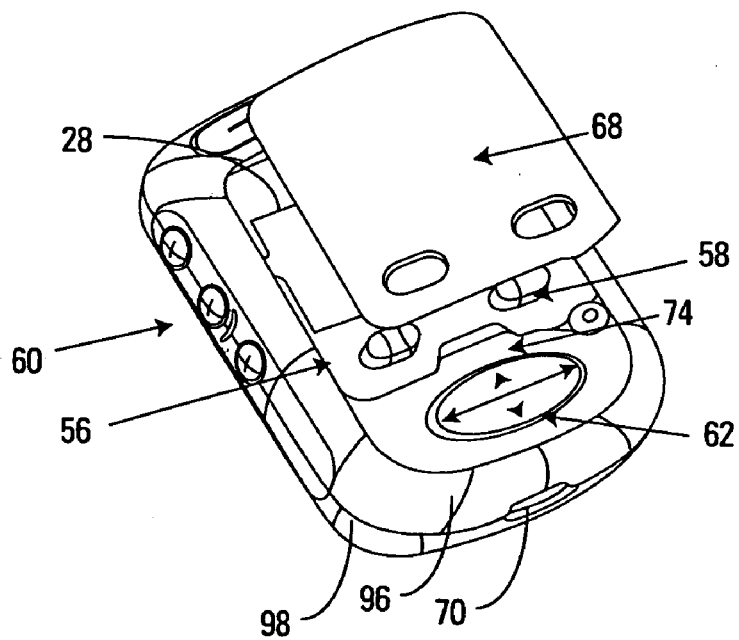
FIG. 5 is a partially exploded view of a patient programmer.
Figure 17:
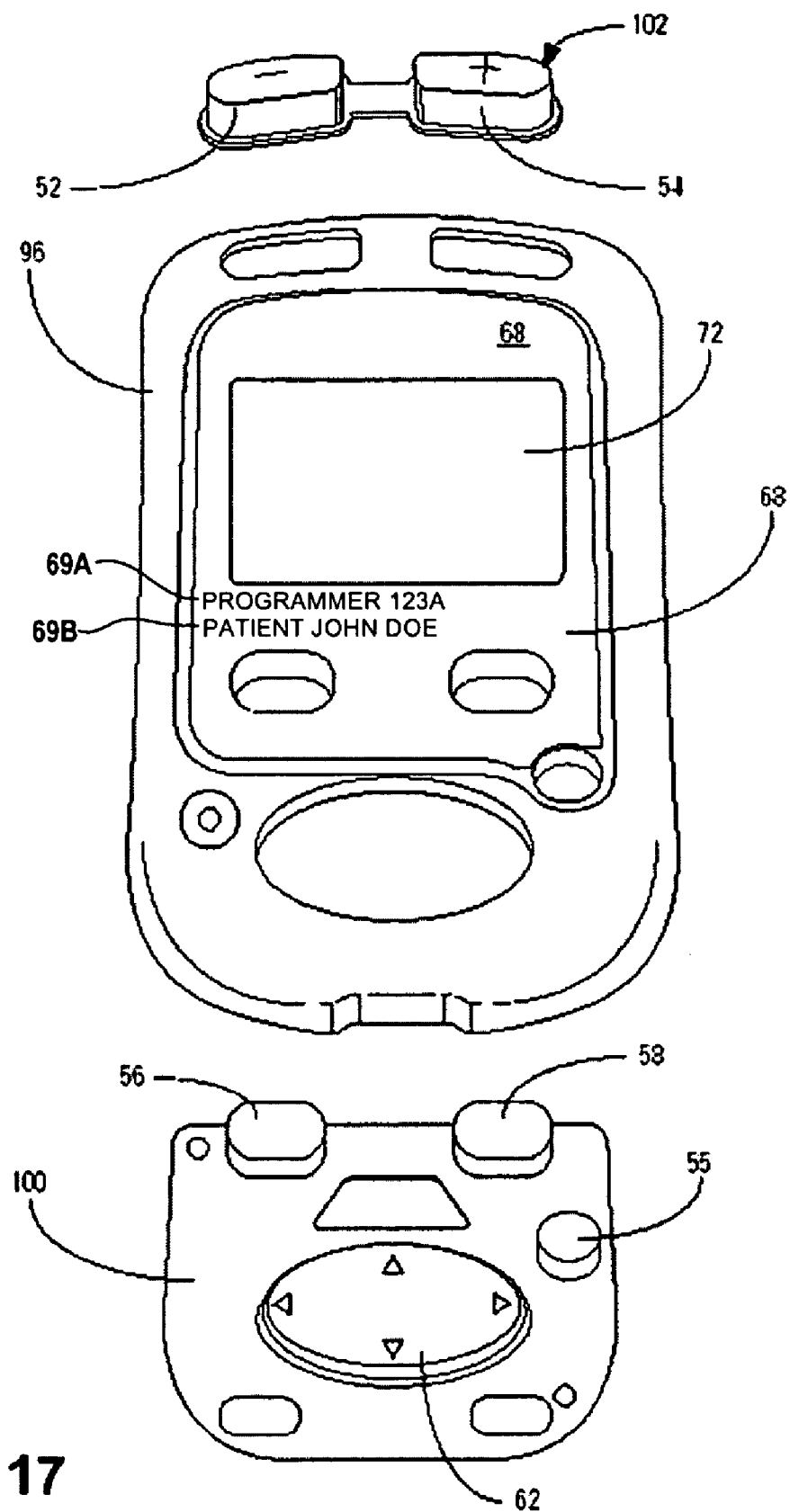
FIG. 17 is a perspective view illustrating an exploded view of the top housing cover including a display lens cover.
Figure 18:
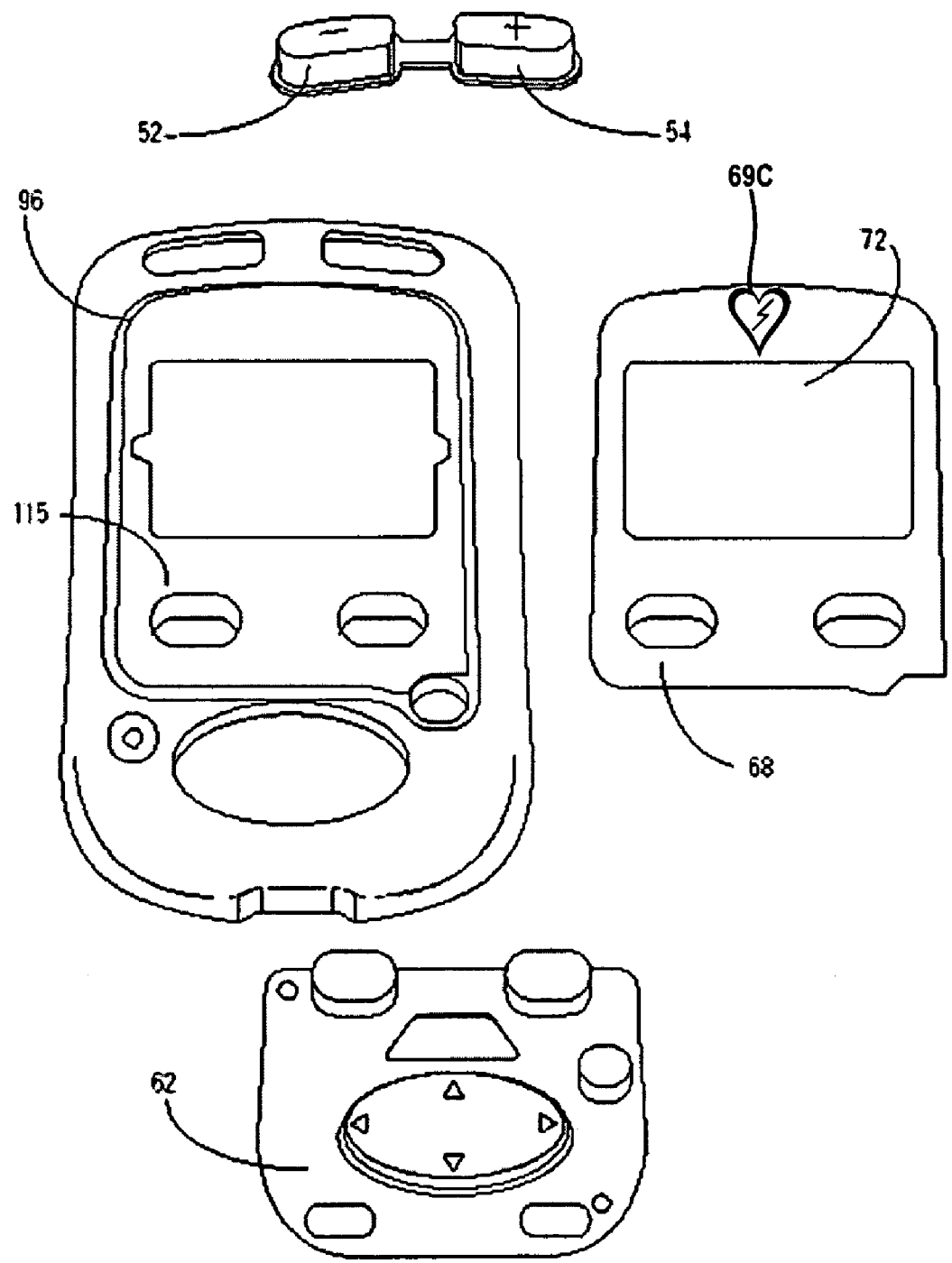
FIG. 18 is a perspective view illustrating another exploded view of the top housing cover with the display lens cover removed from the top housing cover.

FIG. 5 is a partially exploded view of a patient programmer 20 of FIG. 4. As shown in FIG. 4, lens cover faceplate 68 includes apertures to accommodate buttons 56, 58. Again, faceplate 68 may be formed from a clear plastic material. However, a portion of faceplate 68 may be printed to frame a transparent area 72 that exposes display 28 for viewing by the user. Faceplate 68 may be printed with personalization information used to identify a patient or a clinic (e.g., as shown in FIG. 17). Further, faceplate 68 may be printed with graphics or text to match the type of IMD 12 that patient programmer 20 is programmed to control (e.g. as shown in FIG. 18). Faceplate 68 may be designed to fit a configuration of patient programmer 20. For example, faceplate 68 may include additional apertures or no apertures to accommodate the number of buttons included on patient programmer 20. Also, faceplate 68 may be a specific size and/or shape to fit the allotted area within front cover 96.

A software loading interface 74, such as a JTAG interface, is provided within patient programmer 20 under faceplate 68. Front housing cover 96 defines an aperture for access to software loading interface 74. Software loading interface 74 of FIG. 5 may correspond to software loading interface 40 of FIG. 2. Accordingly, patient programmer 20 may be almost fully assembled, except for insertion of faceplate 68, before software loading. Prior to insertion of faceplate 68, the embedded operating system in patient programmer 20 may be loaded, updated, or upgraded via software loading interface 74. A programming device (not shown) may be applied to loading interface 74 via front cover 96 to load the software instructions selected based on the function desired for programmer 20.

One advantage of that configuration is the ability to pre-manufacture patient programmers. A plurality of generic patient programmers may be manufactured and stored until a specific type of programmer 20 is ordered for a particular IMD 12. The generic patient programmers are then programmed with the software appropriate for a desired type of IMD 12 via software loading interface 74. Faceplate 68 conforming to the configuration of patient programmer 20 and the type of IMD 12 is then placed within front cover 96, such that the transparent area 72 exposes display 28 and software loading interface 74 is covered.

For example, software loading interface 74 may be exposed via a front housing cover 96, e.g., prior to place of a lens cover faceplate over the front housing cover. The front housing cover 96 presents an aperture that permits access to the software loading interface 74, but is covered by the lens cover faceplate 68 when it is placed in the front cover housing. In this manner, patient programmer 20 may be programmed as one of the final steps in the manufacturing process. A programming head (not shown) may be sized and shaped to engage the software loading interface 74 and download software from a host computer such as a handheld computing device.

Again, this feature enables a large number of programmers to be preassembled, placed in storage if desired, and then programmed for operation with an appropriate type of neurostimulator, e.g., just before the lens cover faceplate is placed in the front housing cover. Hence, large numbers of programmers 20 can be stockpiled, and then loaded with appropriate operating system and application software to specially configure the programmer for use with a specific neurostimulator.

Programmer 20 also includes infrared interface 70 to receive software changes after programmer 20 has been fully assembled. Infrared interface 70 may correspond to IRDA interface 38 of FIG. 2. Bottom cover 98 and front cover 96 form an aperture to allow access to infrared interface 70. A controller may control infrared interface 70 to initiate an infrared communication session for a period of time, such as approximately 5 to 10 seconds, following power-up of programmer 20. If an infrared source is applied to infrared interface 70 during the period of time immediately following power-up, the controller maintains the infrared communication session until the software changes are uploaded. Hence, upon power-up of programmer 20, e.g. by replacement of batteries or activation of an "on" button, infrared interface 70 is powered up and enters a short listening period to establish communication with a field programmer, if present.

The field programmer may be a PDA with its own infrared port, and may be equipped to download software changes to programmer 20 via infrared interface 70. If no external infrared interface is detected before the end of the short listening period, infrared interface 70 is deactivated. The software changes may include changes to the operating system of the programmer 20, and changes to the neurostimulation programs of IMD 12. In general, the IRDA standard facilitates the point-to-point or point-to-multipoint communication between electronic devices such as computers, mobile phones, and other devices.

In some embodiments, infrared interface 70 may be generally compliant with the IrDA Serial Infrared Physical Layer Specification (IrPHY) Version 1.3 (Oct. 15, 1998). Infrared interface 70 may implement the Low-Power Option and be hardware-limited to a maximum baud rate of 38.4 kilobits per second. Communication relies on a directed infrared communications link over a relatively short distance, on the order of less than or equal to approximately 1 meter. Infrared interface 70 includes an infrared transmitter and receiver for two-way communication with another device.

In the event programmer 20 is a patient programmer, the other device may be a clinician programmer or a dedicated field programmer such as a PDA with an infrared interface, or programmer 20 may communicate with both devices. Upon power-up, infrared interface 70 detects whether a clinician programmer, field programming device, or other device is in the vicinity of programmer 20. If so, programmer 20 establishes communication to update software or firmware within the programmer.

Figure 6A:
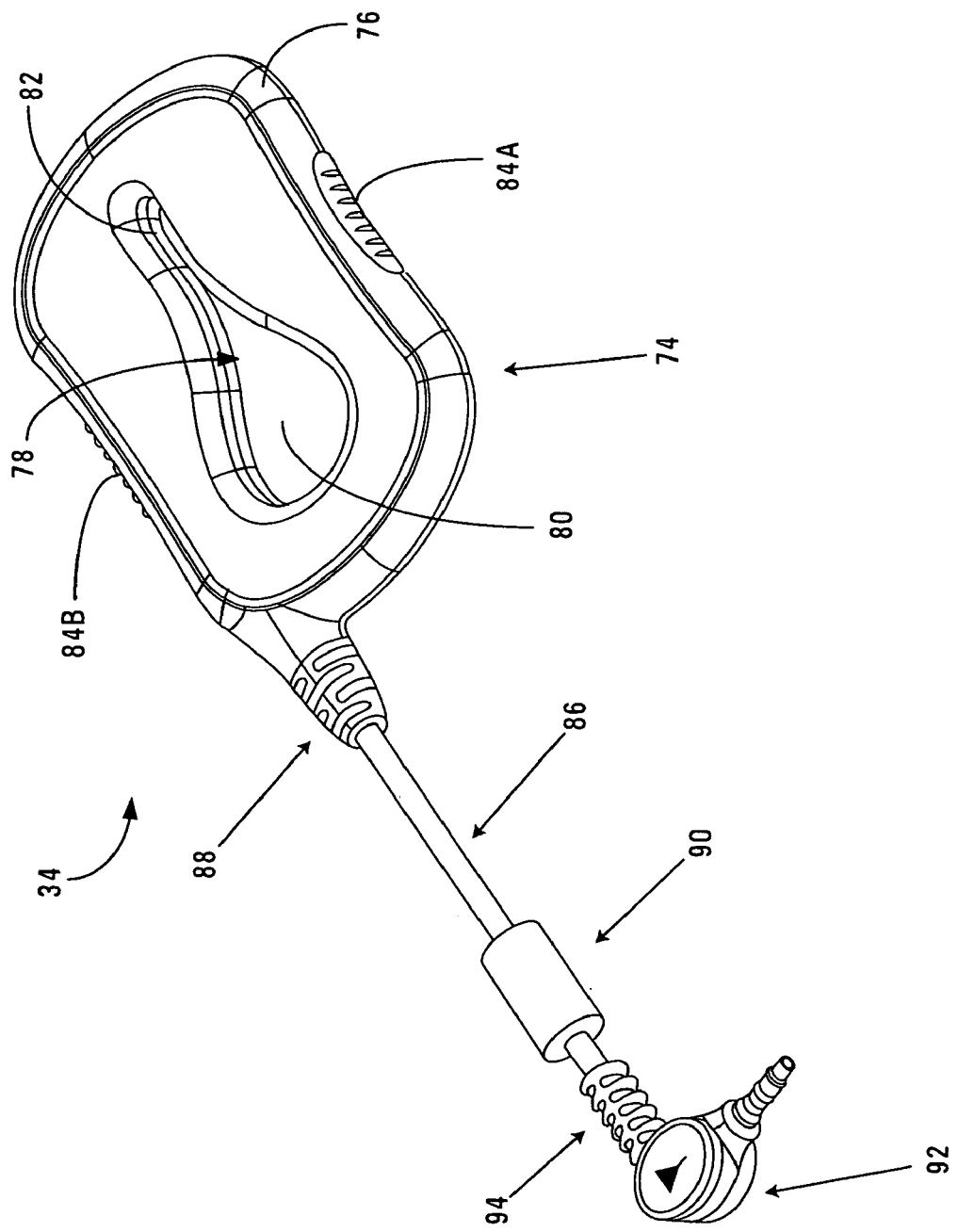
FIG. 6A is a perspective view of an external antenna for use with a patient programmer.

FIG. 6A is a perspective view of an external antenna 34 for use with a patient programmer 20. As shown in FIG. 6A, external antenna 34 includes a cable 86 and a loop-like telemetry head 74 at one end of the cable. The loop-like telemetry head 74 is placed on the patient's body at a position near IMD 12. The loop-like telemetry-head may define a unique aperture 78 with a wide end 80 and a narrow, tapered end 82, e.g., somewhat similar to the shape of a tear drop.

Figure 6B:
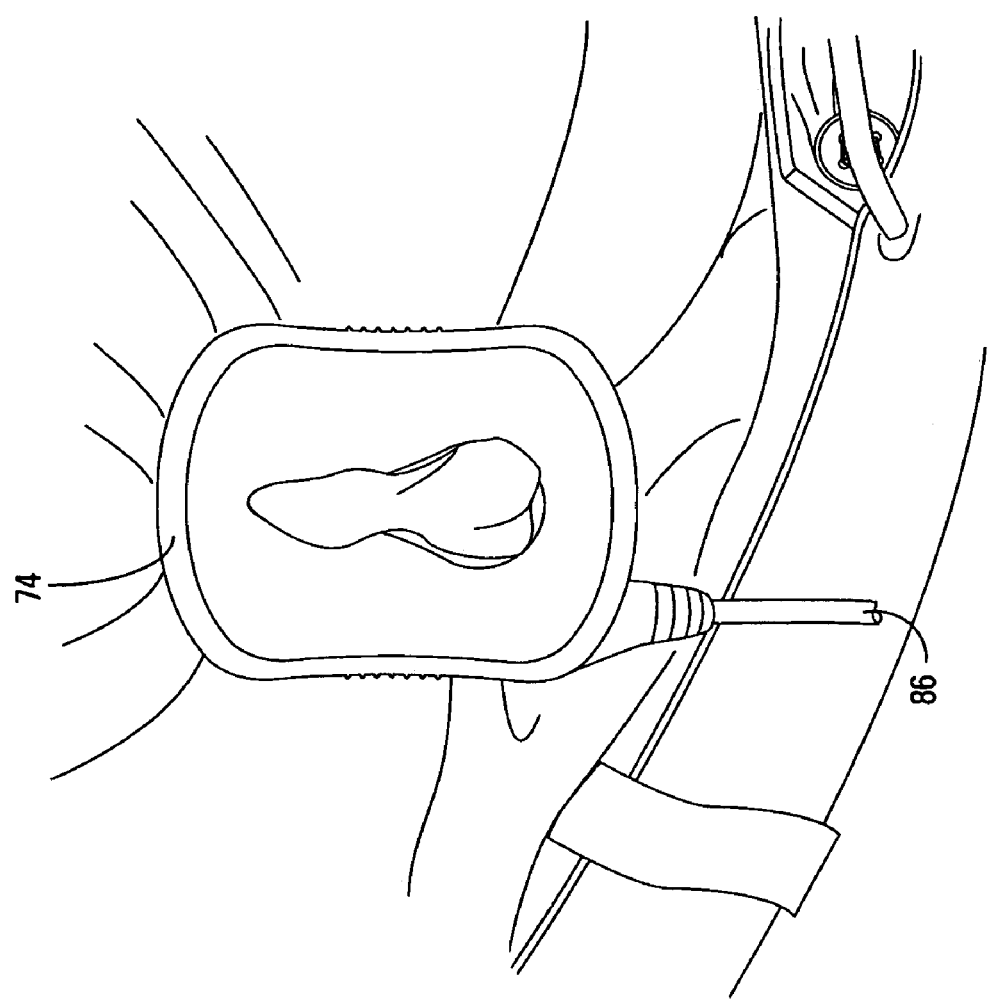
FIG. 6B is a perspective view of an external antenna attached to a patient's shirt.

The narrow, tapered end 82 of the aperture defines a channel or "notch" designed to capture clothing worn by the patient to thereby hold the telemetry head 74 in place near IMD 12 during programming. When the clothing, such as a shirt, is forced into the channel, friction tends to hold the clothing and the telemetry head 74 in place relative to one another. FIG. 6B is a perspective view of telemetry head 74 and cable 86. In FIG. 6B, telemetry head 74 is attached to a patient's shirt. In particular, part of the patient's shirt is held in place within the channel defined by narrow, tapered end 82 to thereby hold telemetry head 74 in place relative to an IMD 12.

The configuration shown in FIGS. 6A and 6B allows relatively stable positioning of external antenna 34 relative to IMD 12. Patient 18 does not need to physically hold external antenna 34 in position relative to IMD 12. Therefore, patient 18 may have both hands free to manipulate programmer 20, update neurostimulation programs, change neurostimulation parameters in IMD 12, or handle other tasks.

As further shown in FIGS. 6A and 6B, telemetry head 74 may be formed from molded plastic 76 and include rubberized grip surfaces 84A, 84B. Cable 86 may include strain relief sections 88, 94, a filter 90, and a plug 92 for plugging the cable into a jack provided in patient programmer 20. The jack provided by programmer 20 also couples external antenna 34 to telemetry interface 30, from FIG. 2. Cable 86 carries a conductor that couples to a conductive antenna loop within telemetry head 74. In FIG. 6A, cable 86 appears to be relatively short but can be approximately two to three feet long if desired. The length of cable 86 allows programmer 20 to perform telemetry via external antenna 34 with display 28 enabled. The distance between external antenna 34 and display 28 reduces interference to telemetry generated by display 28.

Figure 7:
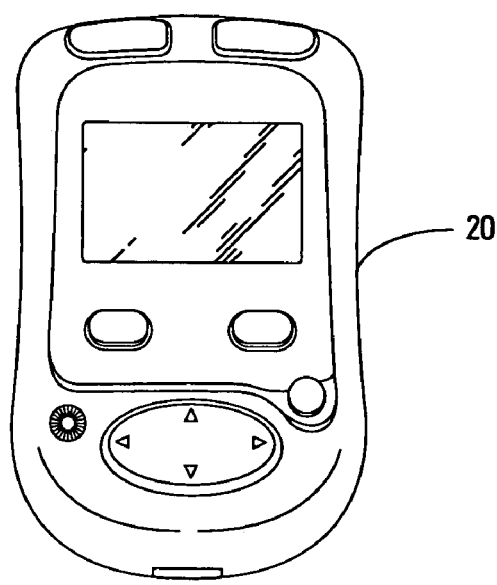
FIG. 7 is a perspective view of a patient programmer.

FIG. 7 is a perspective view of patient programmer 20. Patient programmer 20 is designed to appear similar to a pager or other common, small electronic device, and not necessarily like a medical device. Patient 18 may discreetly carry and use programmer 20. An internal antenna 32 (not shown in FIG. 7) further allows patient 18 to modify the performance of IMD 12 by simply holding programmer 20 in a position relative to IMD 12. In that way, patient 18 is not required to carry an external antenna 34 at all times.

Figure 8:
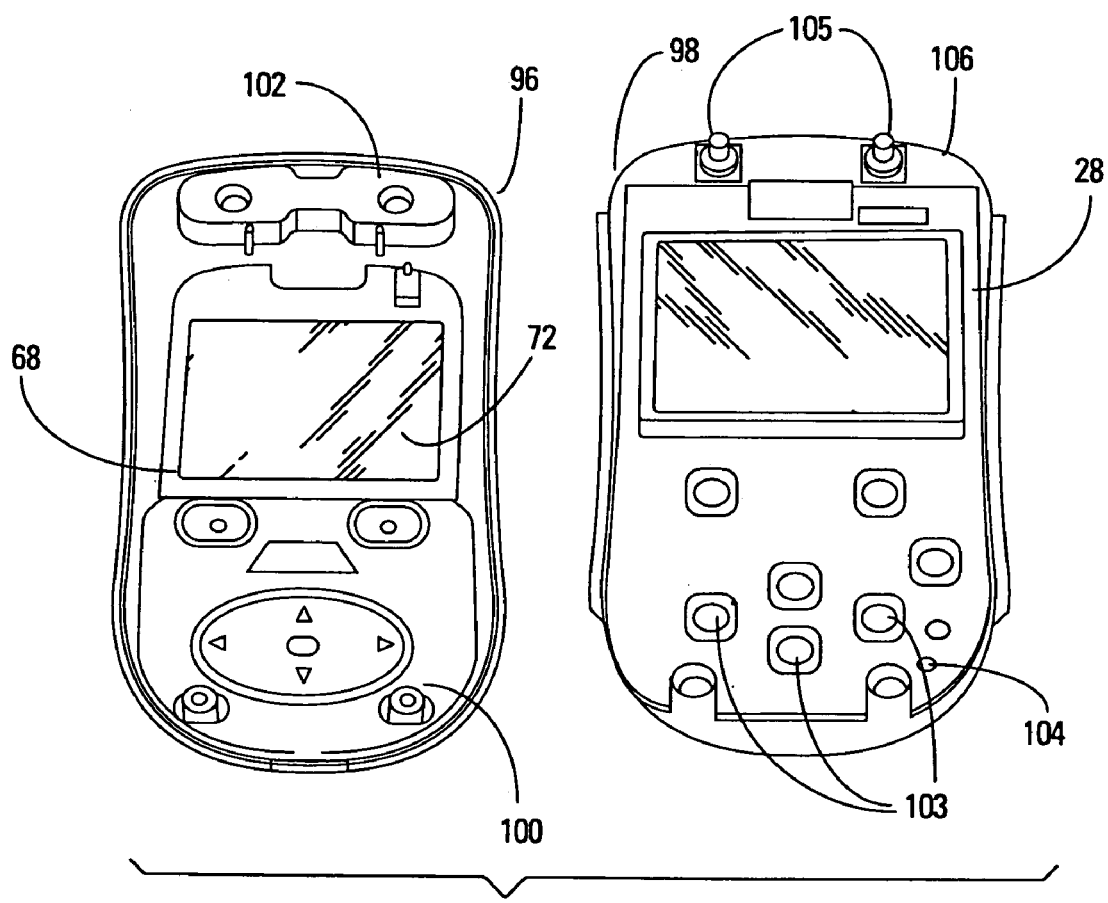
FIG. 8 is a perspective view illustrating the patient programmer of FIG. 7 with the top housing cover removed and an interior view of the top housing cover.

FIG. 8 is a perspective view illustrating the patient programmer 20 of FIG. 7 with the front cover 96 removed and an interior view of the top housing cover. As shown in FIG. 8, bottom cover 98 contains a display circuit board 104 and an antenna circuit board 106 stacked on top of one another. Display circuit board 104 carries display 28 and associated display electronics. In addition, display circuit board 104 carries a number of user input switches 103 that correspond to a push button matrix 26, from FIG. 2.

The input switches 103 receive input from various buttons 55, 56, 58, 60, 62. The buttons may be formed in part by rubber button molding 100, placed between display circuit board 104 and front cover 96, that interfaces with the switches. Input switches 105 are carried by antenna circuit board 106, and interface with button molding 102. Button molding 102 forms buttons 52 and 54 which allow control of the stimulation amplitude. Switches 103 may be formed as conventional snap dome switches.

Front cover 96 includes an aperture 72 to allow a user to view display 28 mounted on display circuit board 104. Front cover 96 also includes an aperture to allow access to software loading interface 74. In the embodiment shown in FIG. 9, button molding 100 also includes an aperture for software loading interface 74. In other embodiments, button molding 100 may comprise a different configuration and number of buttons than that shown in FIG. 9.

Figure 9:
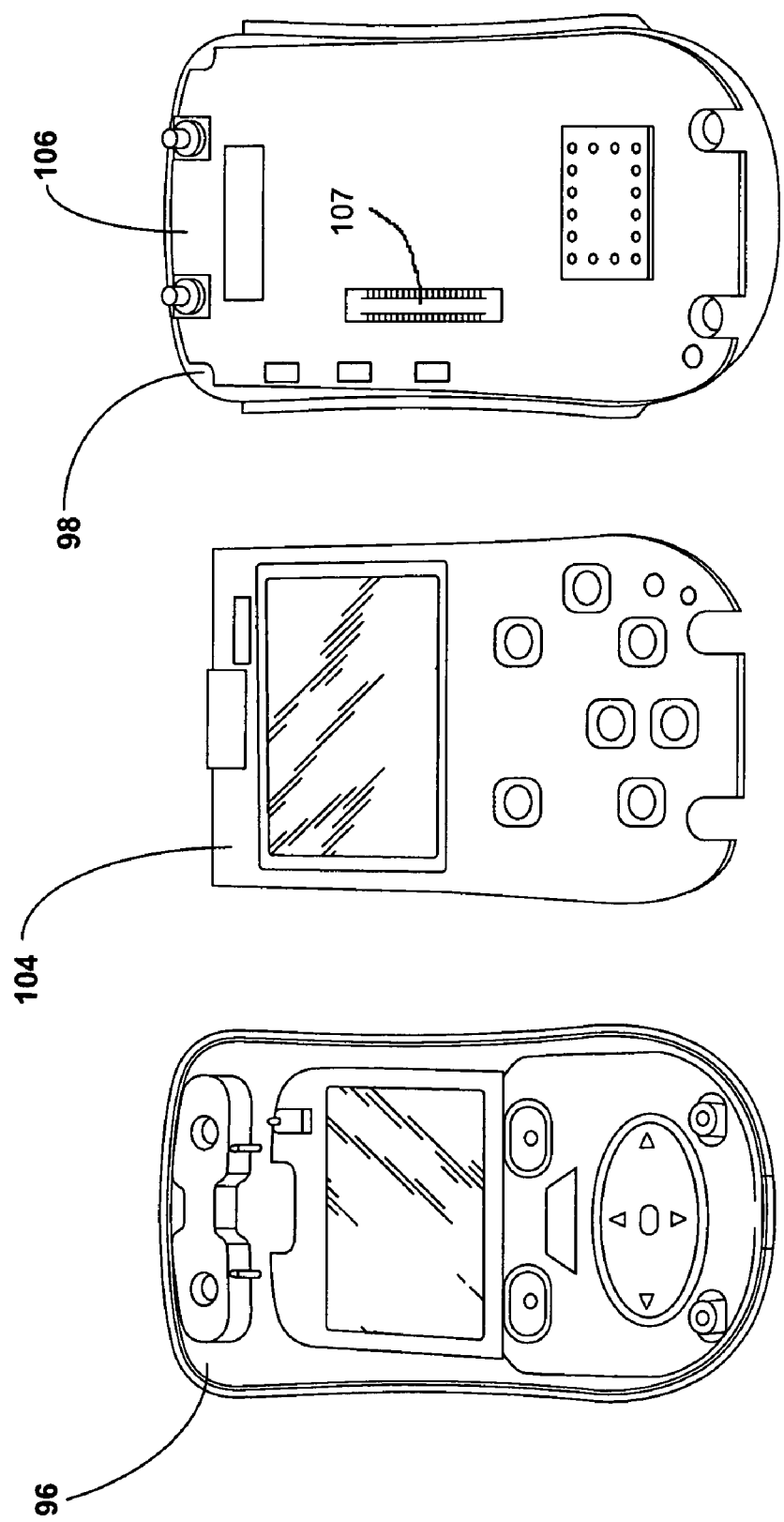
FIG. 9 is a perspective view illustrating the patient programmer of FIG. 7 with the top housing cover and display circuit board removed.

FIG. 9 is a perspective view illustrating the patient programmer of FIG. 7 with the top housing cover 96 and display circuit board 104 removed. FIG. 9 reveals an antenna circuit board 106 that lies beneath display circuit board 104. A connector 107 included on a top side of antenna circuit board 106 serves to connect antenna circuit board 106 to display circuit board 104 via another connector (not shown) included on a bottom side of display circuit board 104.

Antenna circuit board 106 may carry telemetry circuit electronics, power management electronics and, on a bottom side, internal antenna 32. Display circuit board 104 may carry control circuitry, display circuitry electronics, and on a top side, display 28. Antenna circuit board 106 provides power to display circuit board 104 via electrical connector 107.

In some embodiments, the control circuitry on display circuit board 104 controls display 28 and the telemetry circuit electronics on antenna circuit board 106 via connector 107. Hence, the intelligence to control operations of both display circuit board 104 and antenna circuit board 106 may be mounted on a single one of the boards, such as display circuit board 104. The intelligence, in the form of a processor, logic circuitry of other equivalent structure, may interact with components on both boards 104, 106 via electrical connector 107.

Consequently, software may be initially loaded via software loading interface 74, as described herein, to program a processor on only one of the boards 104, 106, such as display circuit board 104. In some embodiments, a processor on display circuit board 104 may be programmed for use with particular types of IMDs, or for use with different antenna circuit boards 106 have different features. In this manner, display circuit board 104 may be generically constructed for modular use in a variety of programmers, but then specifically programmed for a given application.

Internal antenna 32 is placed as far away from display 28 as possible within the reasonable size limits of handheld programmer 20. However, telemetry via internal antenna 32 can still be adversely impacted by electrical and electromagnetic noise generated by display 28 when it is enabled. Therefore, control circuitry, such as processor 22, may be configured to selectively disable display 28 during telemetry via internal antenna 32, in accordance with the invention.

To further reduce electrical and electromagnetic interference, in some embodiments, display circuit board 104 may be designed to include a majority of digital components, such as display, processor and memory circuitry, and antenna circuit board 106 may be designed to include a majority of analog components, such as telemetry and power supply circuitry. In either case, the control circuitry may selectively disable display circuit board 104 during telemetry via internal antenna 32 to substantially eliminate digital noise associated with display 28.

Figure 10:
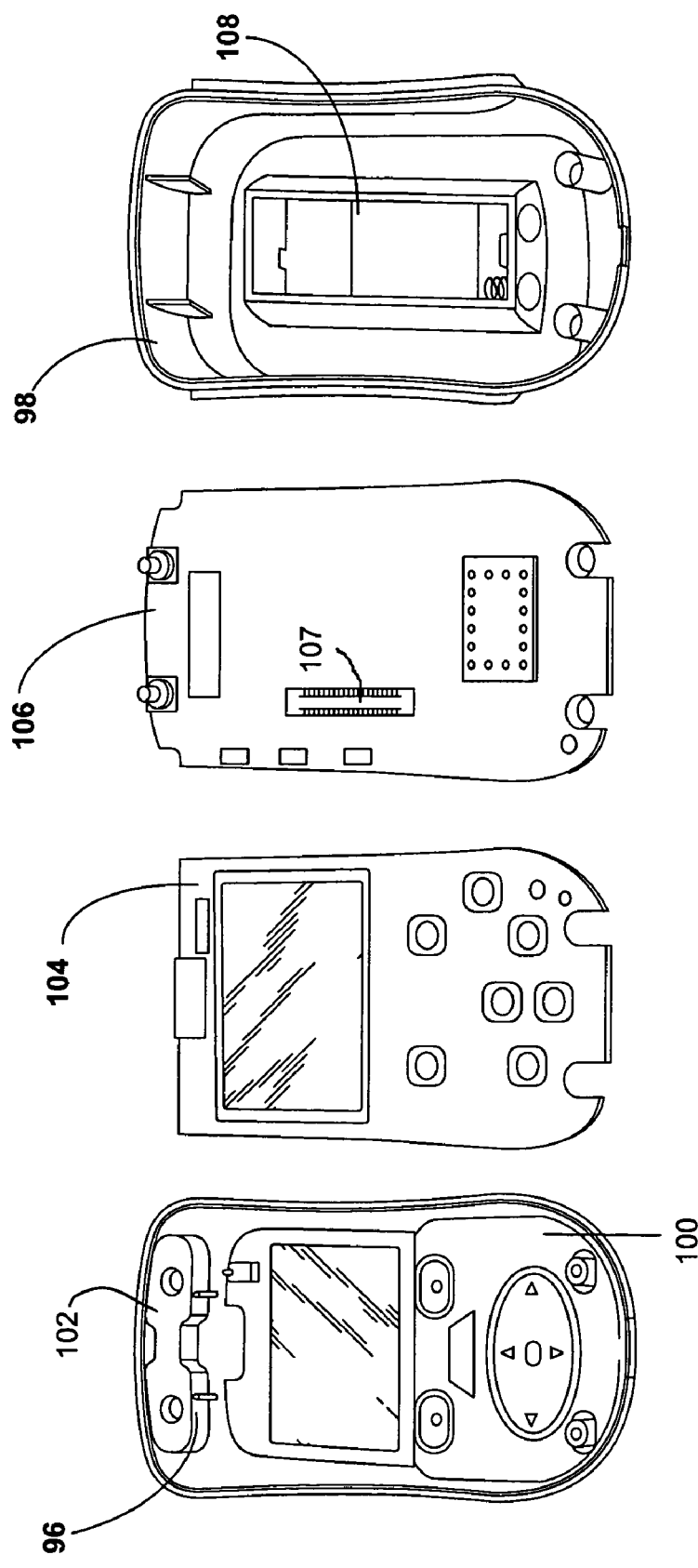
FIG. 10 is a perspective view illustrating the patient programmer of FIG. 7 with the top housing cover, display circuit board and antenna circuit board removed.

FIG. 10 is a perspective view illustrating the patient programmer of FIG. 7 with the top housing cover 96, display circuit board 104 and antenna circuit board 106 removed. As shown in FIG. 10, bottom cover 98 defines a battery bay 108. Battery bay 108 may be formed by a rectangular raised wall that is molded into bottom cover 98. Battery bay 108 may be shaped and sized to accommodate one or more batteries to power the components in patient programmer 20. In the embodiment shown in FIG. 10, battery bay 108 is sized to accommodate two AAA alkaline batteries for purposes of illustration. The rectangular raised wall protrudes into patient programmer 20 such that the wall and the batteries in battery bay 108 are substantially adjacent to a bottom side of antenna circuit board 106. Battery bay 108 is entirely contained within patient programmer 20, and consumes some of the depth of the patient programmer housing.

As shown in FIG. 10, in accordance with the invention, patient programmer 20 may be assembled by stacking components 98, 106, 104, 96 on top of one another in a z-axis technique. The z-axis technique allows the assembly process to be at least partially automated, and generally refers to the stacking of components, one on top of the other, from bottom to top. For example, antenna circuit board 106 is placed into bottom housing cover 98.

Display circuit board 104 is then placed over antenna circuit board 106 and coupled to antenna circuit board 106 via electrical connector 107. Front cover 96 is placed over display circuit board 104 to substantially enclose the display and antenna circuit boards 104, 106 within front cover 96 and bottom housing cover 98. In some embodiments, the placement of button moldings 100, 102 over display circuit board 104 prior to the placement of front cover 96 is also automated. After programmer 20 is substantially assembled, as described above, software is loaded into a memory 24 via software loading interface 40 through an aperture in front cover 96. A faceplate 68 is then placed over front cover 96 to cover loading interface 40 and expose display 28 for viewing, providing a complete assembly.

Figure 11:
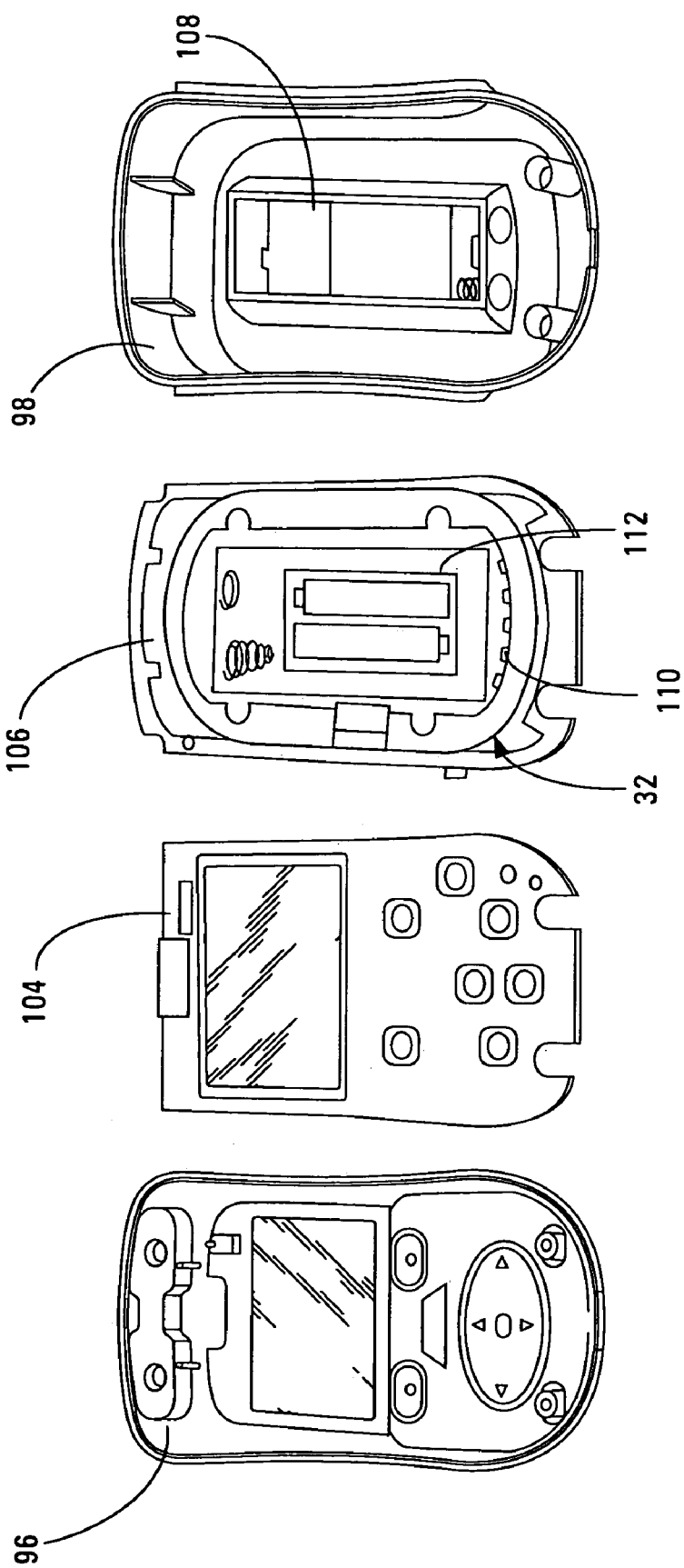
FIG. 11 is a perspective view illustrating the patient programmer of FIG. 7 with the top housing cover, display circuit board and antenna circuit board removed, and an antenna-side view of the antenna circuit board.

FIG. 11 is a perspective view illustrating the patient programmer of FIG. 7 with the top housing cover 96, display circuit board 104 and antenna circuit board 106 removed, and an antenna-side view of the antenna circuit board, i.e., a view of the antenna circuit board from a side on which the antenna is mounted. As shown in FIG. 11, antenna circuit board 106 carries internal antenna 32. Internal antenna 32 may have a loop-like structure 110 that defines a central aperture 112. In some embodiments, the loop-like structure 110 may be substantially rectangular. The central aperture 112 may be shaped and sized to permit insertion of one or more batteries placed in battery bay 108 of bottom housing cover 98. Battery bay 108 may protrude into the antenna aperture 112 when programmer 20 is fully assembled. The batteries may rest on the surface of antenna circuit board 106.

The batteries may be placed in the battery bay via an access door on the outside of the patient programmer housing. The access door may be a hinged door or a removable, sliding door. In some cases, the batteries in battery bay 108 may contribute favorably to the RF load presented to the internal antenna 32. In particular, the batteries contained within loop-like structure 110 may present an additional load to the internal antenna 32 that enhances immunity to electrical and electromagnetic interference from external magnetic fields during telemetry sessions with the IMD 12. To further reduce electrical and electromagnetic interference, the internal antenna 32 may be constructed with a woven copper braid that enhances shielding and reduces antenna loading during transmission and reception.

Figure 12:
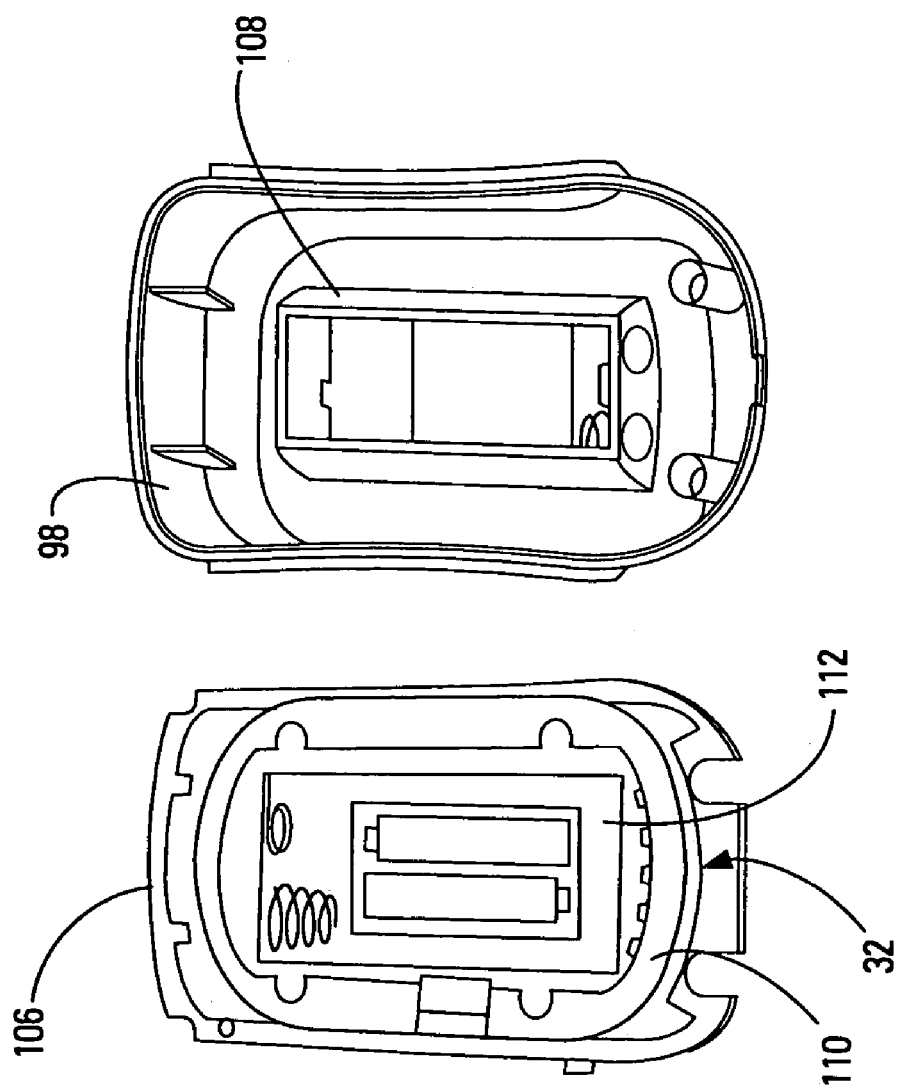
FIG. 12 is a perspective view illustrating the antenna circuit board and bottom housing cover of the patient programmer of FIG. 7.

FIG. 12 is a perspective view illustrating the antenna circuit board 106 and bottom housing cover 98 of the patient programmer 20 of FIG. 7. Internal antenna 32 is mounted away from antenna circuit board 106 to maximize the distance between internal antenna 32 and display 28 mounted on display circuit board 104. In some embodiments, antenna 32 may be securely mounted within an annular, recessed area in bottom housing cover 98 that surrounds battery bay 108.

For example, antenna 32 may be mounted on a carrier that is welded to bottom housing cover 98. The space between antenna circuit board 106 and loop-like structure 110 is substantially filled by battery bay 108 extending into antenna aperture 112. The placement of battery bay 108 within aperture 112 enables programmer 20 to maintain a smaller size. Also, the batteries placed in battery bay 108 within aperture 112 reduce external magnetic interference to internal antenna 32 by providing an RF load to the internal antenna, enhancing noise immunity.

Figure 13:
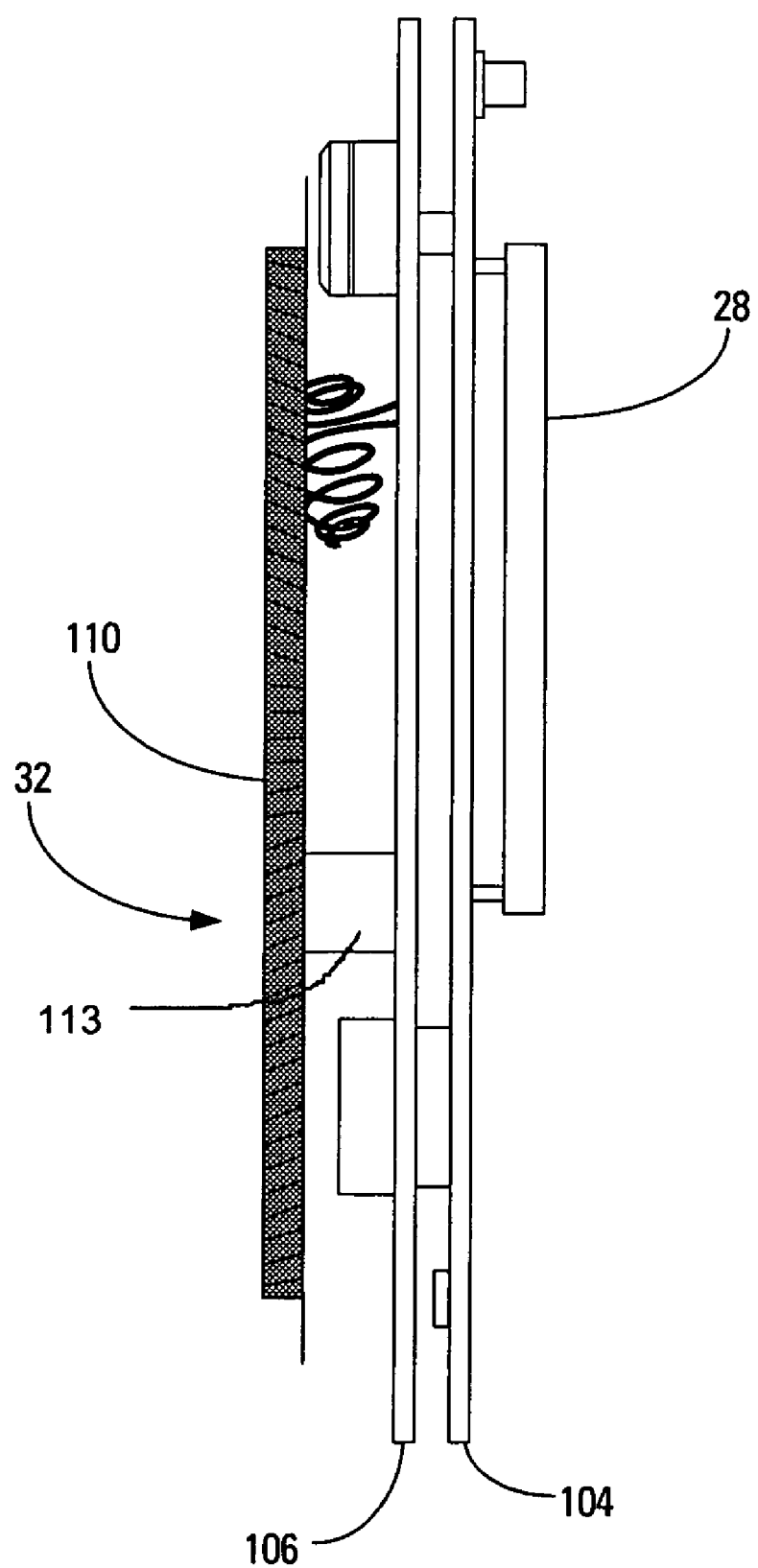
FIG. 13 is a perspective view illustrating a side view of the display circuit board and the antenna circuit board.
Figure 14:
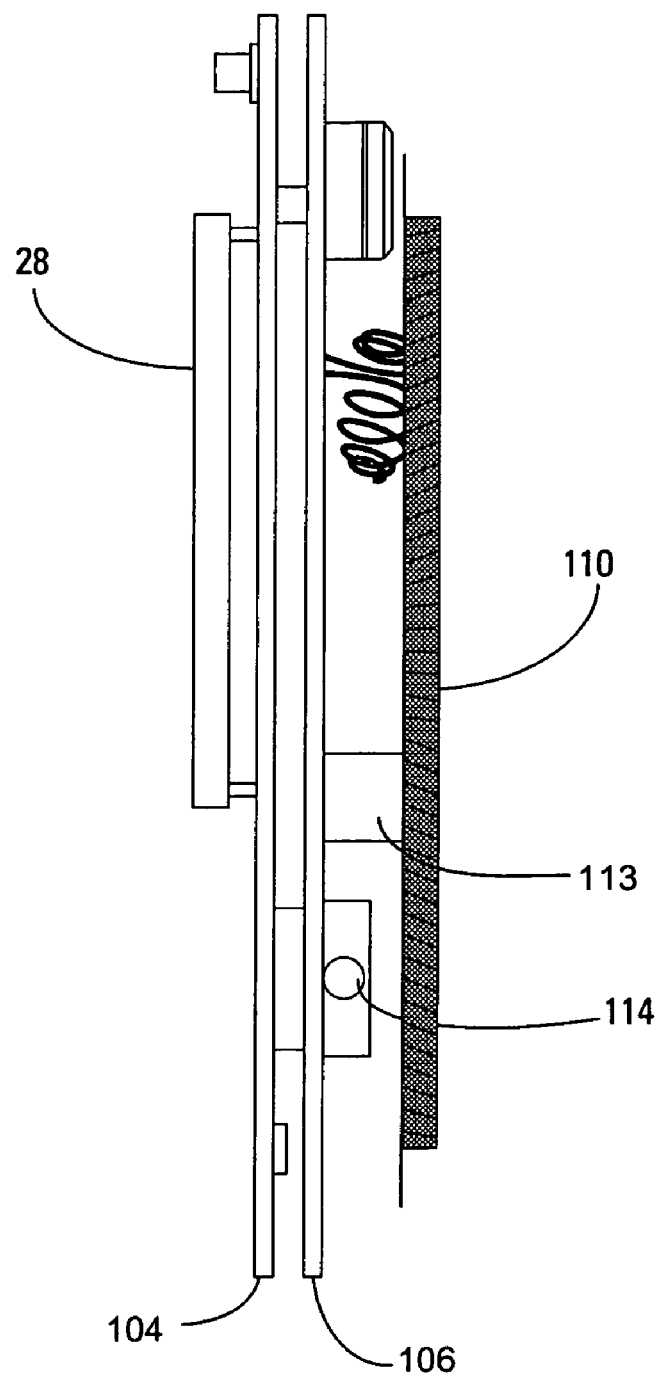
FIG. 14 is a perspective view illustrating a second side view of the display circuit board and the antenna circuit board.

FIG. 13 is a perspective view illustrating a side view of the display circuit board 104 and the antenna circuit board 106. FIG. 14 is a perspective view illustrating a second side view of the display circuit board 104 and the antenna circuit board 106. As shown in FIGS. 13 and 14, the loop-like structure 110 of internal antenna 32 is displaced from the surface of antenna circuit board 106. Loop-like structure 110 is mounted to a connector 113 on the surface of antenna circuit board 106. The connector couples internal antenna 32 to telemetry circuitry 30. A jack 114 is provided on antenna circuit board 106 to receive plug 92 from external antenna 34. Jack 114 couples external antenna 34 to telemetry interface 30. Display 28 is mounted to the surface of display circuit board 104 and is coupled to display circuitry.

Display circuit board 104 and antenna circuit board 106 are coupled to each other by an electrical connector interface. The electrical connector interface (not shown) allows the circuitry on the two circuit boards to interact. For example, antenna circuit board 106 includes power control circuitry that powers both circuit boards 104 and 106, as well as telemetry circuitry. The power control circuitry may include a dc-dc converter to convert power from batteries to operating power for the various components within programmer 20.

Additionally, display circuit board 104 includes control circuitry, such as processor 22, to control both display 28 and telemetry interface 30. The control circuitry may selectively disable or enable display 28 and related display circuitry based on whether external antenna 34 is connected to programmer 20 via jack 114. If so, display 28 can be enabled because the electrical and electromagnetic noise generated by the display is less likely to have an adverse effect on telemetry via external antenna 34.

To reduce the effects of electrical and electromagnetic interference produced by display 28, and associated display electronics, on telemetry performance, the display and internal antenna 32 may be displaced from one another within the patient programmer housing, as shown in FIGS. 13 and 14. For example, the display 28 and associated display electronics are mounted on a display circuit board 104, and internal antenna 32 and associated transmit and receive electronics may be mounted on antenna circuit board 106.

The display and antenna circuit boards 104, 106 occupy different planes, displaced from one another, within the housing of patient programmer 20. Hence, processor 22 may be configured to drive telemetry electronics on antenna circuit board 106, yet reside on a different board, e.g., display circuit board 104. However, display 28 and internal antenna 32 may overlap one another, providing a compact, stack-like configuration. Internal antenna 32 may be mounted on an outward-facing side of the antenna circuit board 106, and the display 28 may be mounted on an outward-facing side of the display circuit board 104. The internal antenna may be mounted in bottom housing cover 98 above the surface of the circuit board via a connector. In this manner, the internal antenna also may be displaced from the second circuit board.

The separation distance between the circuit boards 104, 106 may serve to reduce the effects of electrical and electromagnetic interference caused by the display 28 on signals transmitted and received by the internal antenna 32. In addition, the placement of the telemetry electronics and display electronics on different circuit boards may reduce interference. In summary, the internal antenna arrangement provides a compact design, but reduces the effects of circuit board noise on telemetry performance due to operation of display 28.

A majority of digital electronics may be placed on the display circuit board 104 with the display 28, and a majority of analog and RF electronics may be placed on the antenna circuit board 106. Consequently, much of the digital electronics on the display circuit board 104 may be selectively turned off during telemetry sessions administered by analog components on the other circuit board 106.

In some embodiments, for purposes of illustration, the center planes of the display circuit board 104 and the antenna circuit board 106 may be approximately 0.3 to 1.0 cm apart. The internal antenna 32, mounted above antenna circuit board 106, may be approximately 1.0 to 1.5 cm away from the center plane of the display circuit board, and approximately 1.2 to 2.0 cm away from the backplane of display 28. Loop-like structure 110 of internal antenna 32 may have an inner dimension (i.e., of aperture 112) of approximately 5.5 to 6.5 cm in length by approximately 2.8 to 3.2 cm in width, and an outer dimension of approximately 6.5 to 7.5 cm in length by approximately 4.2 to 4.6 cm in width. Display 28 may have a dimension of approximately 3.0 cm by approximately 4.3 cm.

Figure 15:
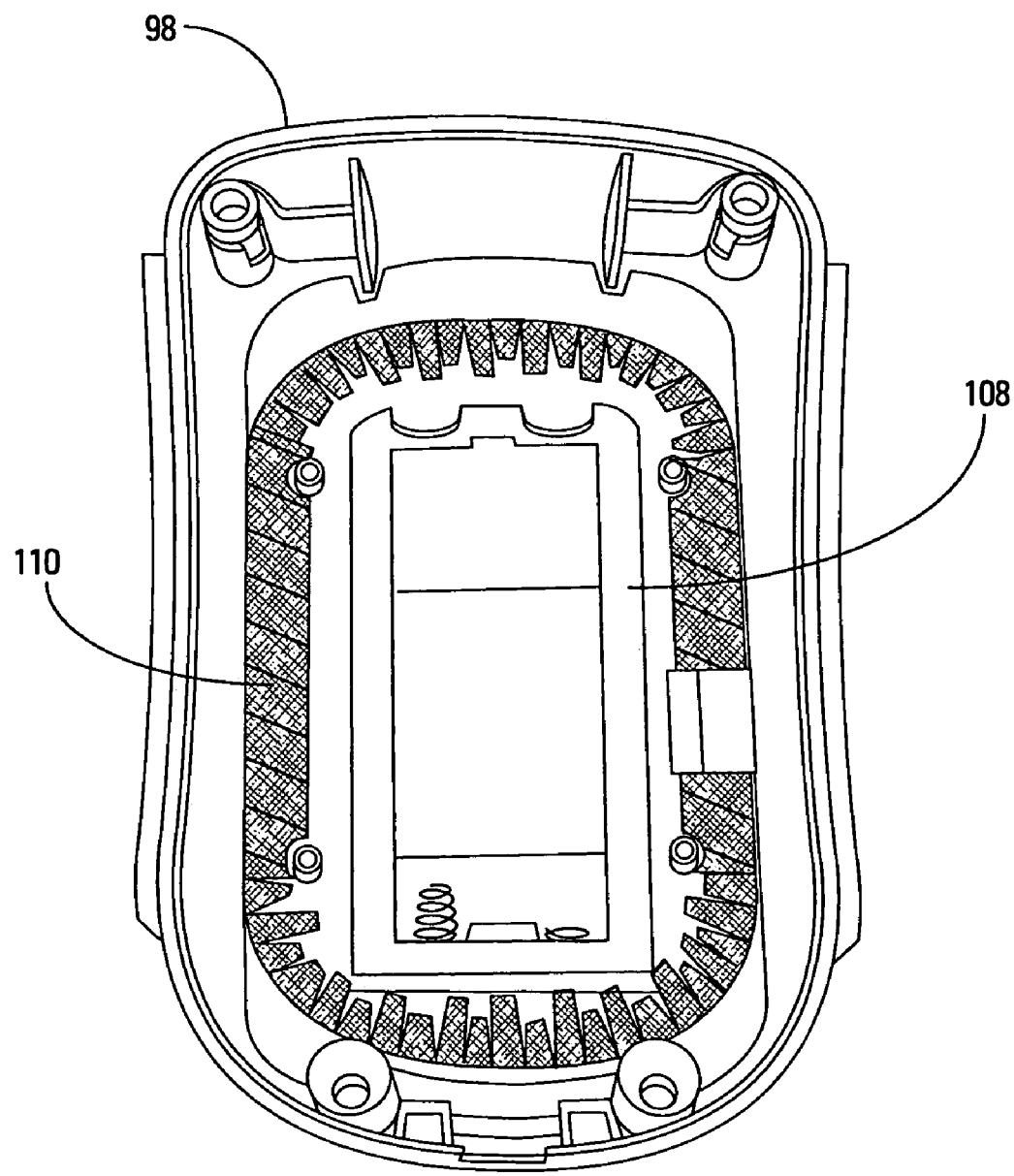
FIG. 15 is a perspective view illustrating the bottom housing cover with a battery bay and an internal antenna.

FIG. 15 is a perspective view illustrating the bottom housing cover 98 with a battery bay 108 and loop-like structure 110 of internal antenna 32. As shown in FIG. 15, loop-like structure 110 extends about the rectangular wall of battery bay 108, and resides in a recess between the outer walls of bottom cover 98 and the battery bay. Thus, battery bay 108, and batteries placed in the battery bay, protrude upward through the aperture defined by loop-like structure 110. Accordingly, the batteries fill a portion of the aperture, and provide an additional load that enhances noise immunity for internal antenna 32.

Figure 16:
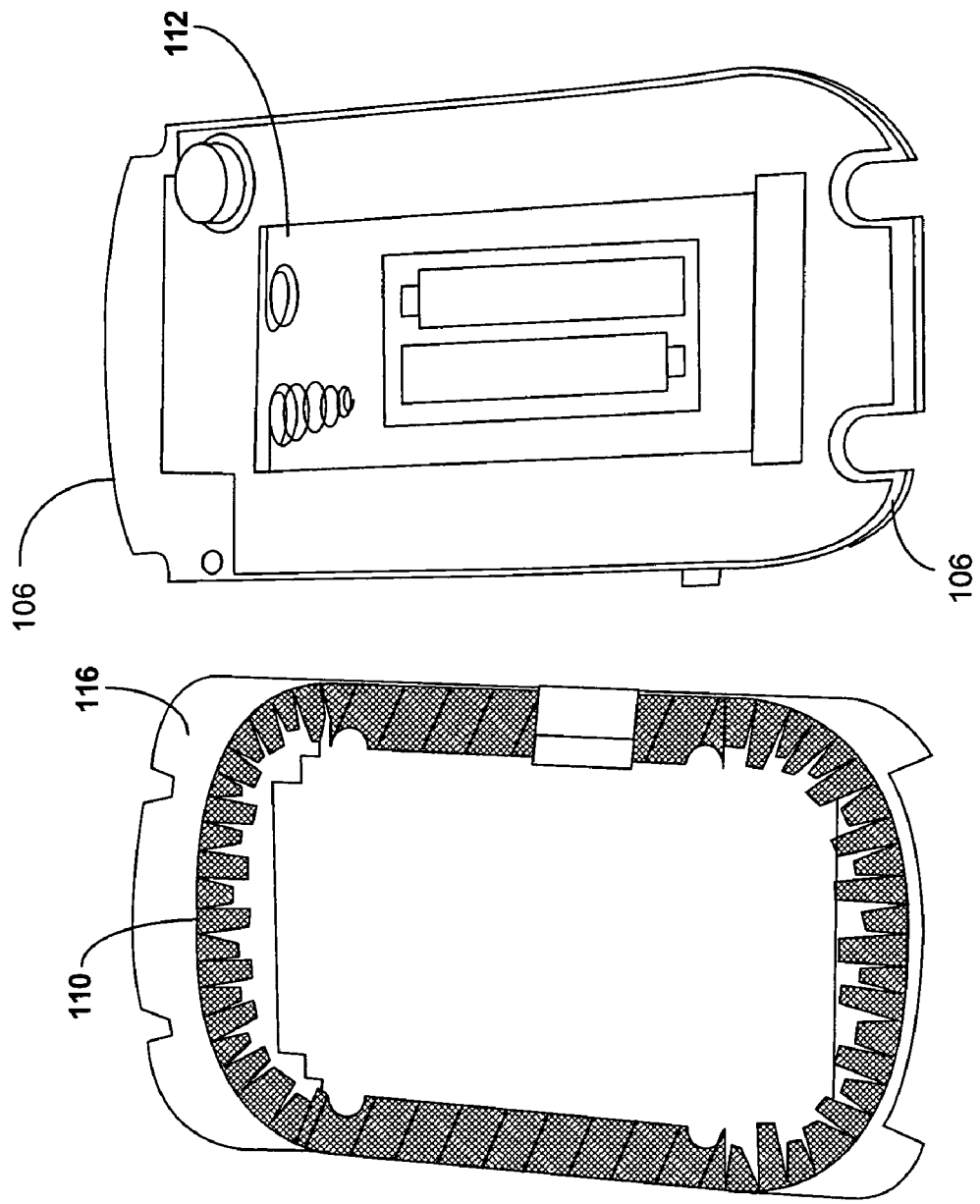
FIG. 16 is a perspective view illustrating the internal antenna and the antenna circuit board.

FIG. 16 is a perspective view illustrating the internal antenna 32 and the antenna circuit board 106. As shown in FIG. 16, antenna 32 may be adhesively bonded to an insulative spacer 116. Internal antenna 32 comprises a plastic frame shaped to fit within bottom cover 98 and around battery bay 108. The plastic frame comprises connector pins to couple to antenna circuit board 106. Conductive windings wrap around the plastic frame to create internal antenna 32. The conductive windings may be wrapped about a perimeter of the plastic frame. The plastic frame and conductive windings are then substantially surrounded by a copper braid shielding that is wrapped in successive turns around the plastic frame and windings to block external magnetic interference.

FIG. 17 is a perspective view illustrating an exploded view of the top housing cover 96 including a display lens cover faceplate 68. Faceplate 68 is formed of transparent plastic material, and is printed to form a non-transparent border around a display screen window 72 that exposes display 28 for viewing by patient 18. Also illustrated are button moldings 100, 102, which carry formed buttons 52, 54, 55, 56, 58, 62.

FIG. 18 is a perspective view illustrating another exploded view of the top housing cover 96 with the display lens cover faceplate removed from the top housing cover. Faceplate 68 may be mounted within a recessed area 115 formed in top cover 96 as the final step in assembly of patient programmer 20. Faceplate 68 may be an in-mold decorated lens faceplate that can be printed with distinctive indicia just prior to assembly to customize the appearance of patient programmer 20, and then inserted into recessed area 115 in the front housing cover 96. Faceplate 68 may also be customized for a number of apertures required for buttons on a particular type of programmer 20. In some cases, the display lens cover faceplate 68 may be printed with personalization information, such as patient name, address and phone number.

Also, the display lens cover faceplate 68 may carry different graphics, such as printed text 69A and 69B (shown in FIG. 17) or printed graphic 69C (shown in FIG. 18), to distinguish different types of therapy delivered by the IMD 12 with which patient programmer 20 is used, distinguish different model types or identify the patient. The faceplate also may be made with different configurations that expose different sets of buttons, and may have different appearances, including different colors, illustrations, and designs, while fitting in a common mounting area defined by recessed area 115. Hence, the faceplate 68 may be selected from one of a plurality of faceplates having different configurations based on a match between the configuration of the plate member and a type of neurostimulator programmer being assembled.

For example, various color schemes, graphical motifs, and the like may be patient-selectable by selecting a particular faceplate 68. The patient may enjoy the ability to choose the appearance of programmer 20 by choosing a faceplate 68. Although a particular faceplate configuration is described and illustrated herein for purposes of illustration, the size, shape and structure of faceplate 68 should not be considered limiting. Rather, faceplate 68 may have any of a variety of different characteristics. Once selected, a particular faceplate 68 may be fixed to the housing of programmer 20, e.g., during manufacturing following a pre-order specification of the faceplate. Alternatively, the faceplate 68 may be readily applied to the housing of programmer 20 and, in some instances, made detachable so that the faceplate may be detached and replaced with a different faceplate, if desired.

The patient programmer 20 may feature a stacked configuration that permits Z-axis assembly of the components of the programmer, including bottom housing cover 98, internal antenna 32, antenna circuit board 106, display circuit board 104, button moldings 100, 102, top housing cover 96, and display lens cover faceplate 68, which protects display 28. In this manner, the various components may be stacked on top of one another to build the patient programmer 20 from back to front, i.e., in a z-axis orientation. The z-axis assembly can simplify assembly, and permit automated assembly techniques in some instances.

Figure 19:
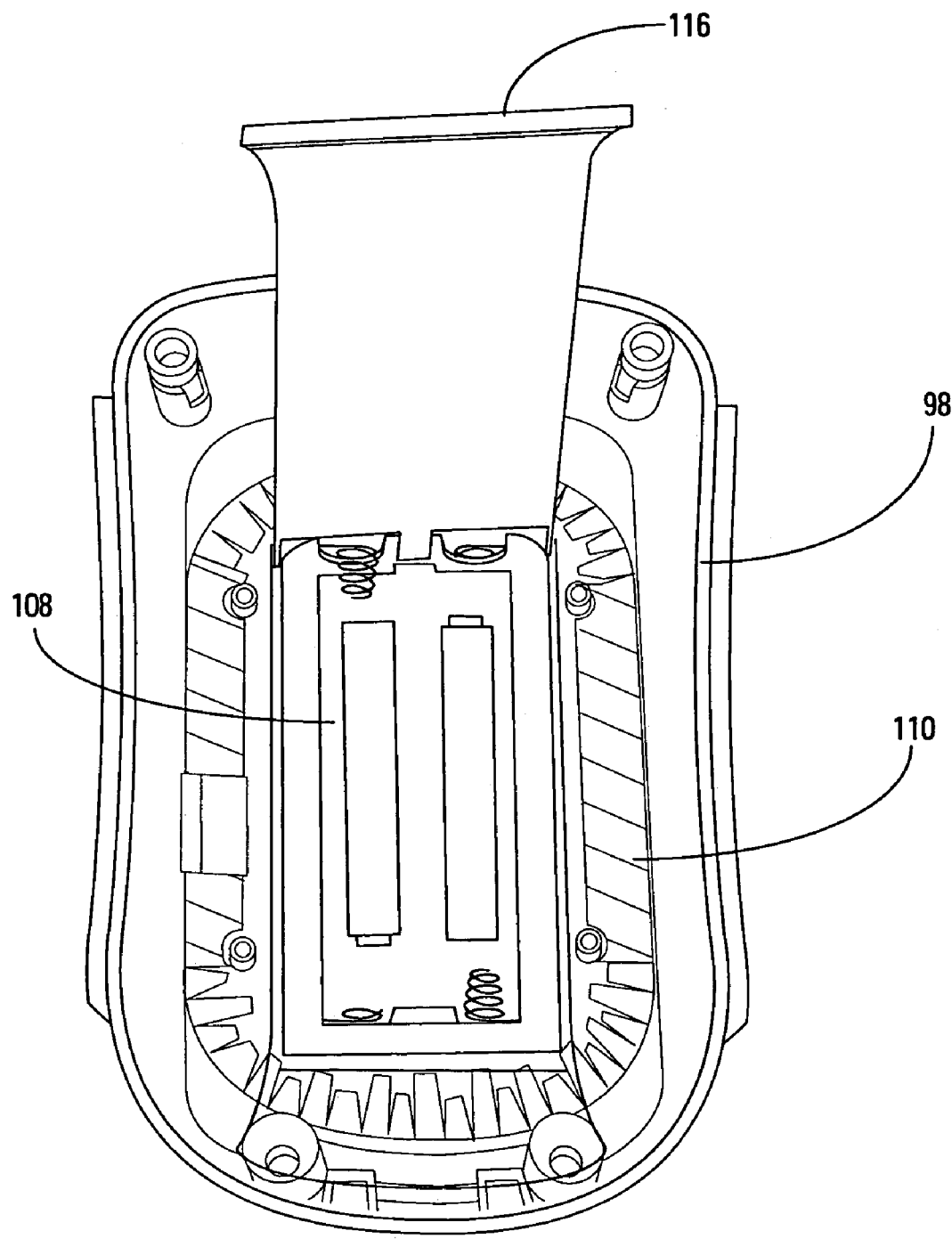
FIG. 19 is a perspective view illustrating a bottom side of the patient programmer of FIG. 7, including a battery door.

FIG. 19 is a perspective view illustrating a bottom side of the patient programmer 20 of FIG. 7, including a battery door. As shown in FIG. 19, bottom cover 98 of patient programmer 20 may include a hinged battery door 116 that provides access to battery bay 108. Accordingly, a patient may replace batteries within battery bay 108 when the batteries are near depletion. A low battery indication may be presented by display 28 in response to detection of a low battery state by power management module 43 (FIG. 2).

Figure 20:
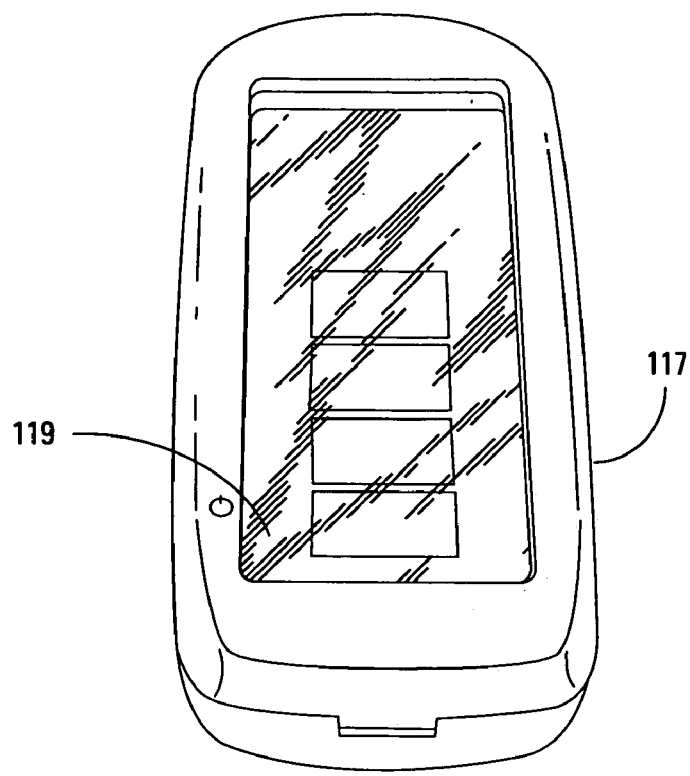
FIG. 20 is a perspective view illustrating a clinician programmer that may be used with a medical device as described herein.
Figure 21:
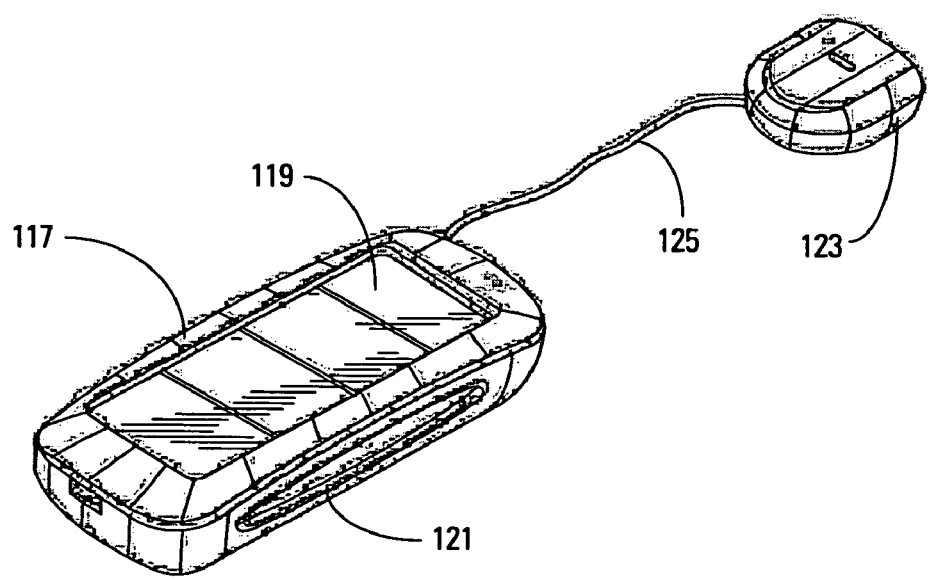
FIG. 21 is a perspective view of the clinician programmer of FIG. 19.

FIG. 20 is a perspective view illustrating a clinician programmer 117, with a touchscreen 119, that may be used with a neurostimulation system 10 as described herein. FIG. 21 is a perspective view of the clinician programmer 117 of FIG. 20, and further illustrates a stylus 121 for use with touchscreen 119, and an RF telemetry head 123 attached to the clinician programmer 117 via a cable 125. In operation, a clinician uses clinician programmer 117 to program neurostimulation therapies into IMD 12 via RF telemetry using RF telemetry head 123.

Figure 22:
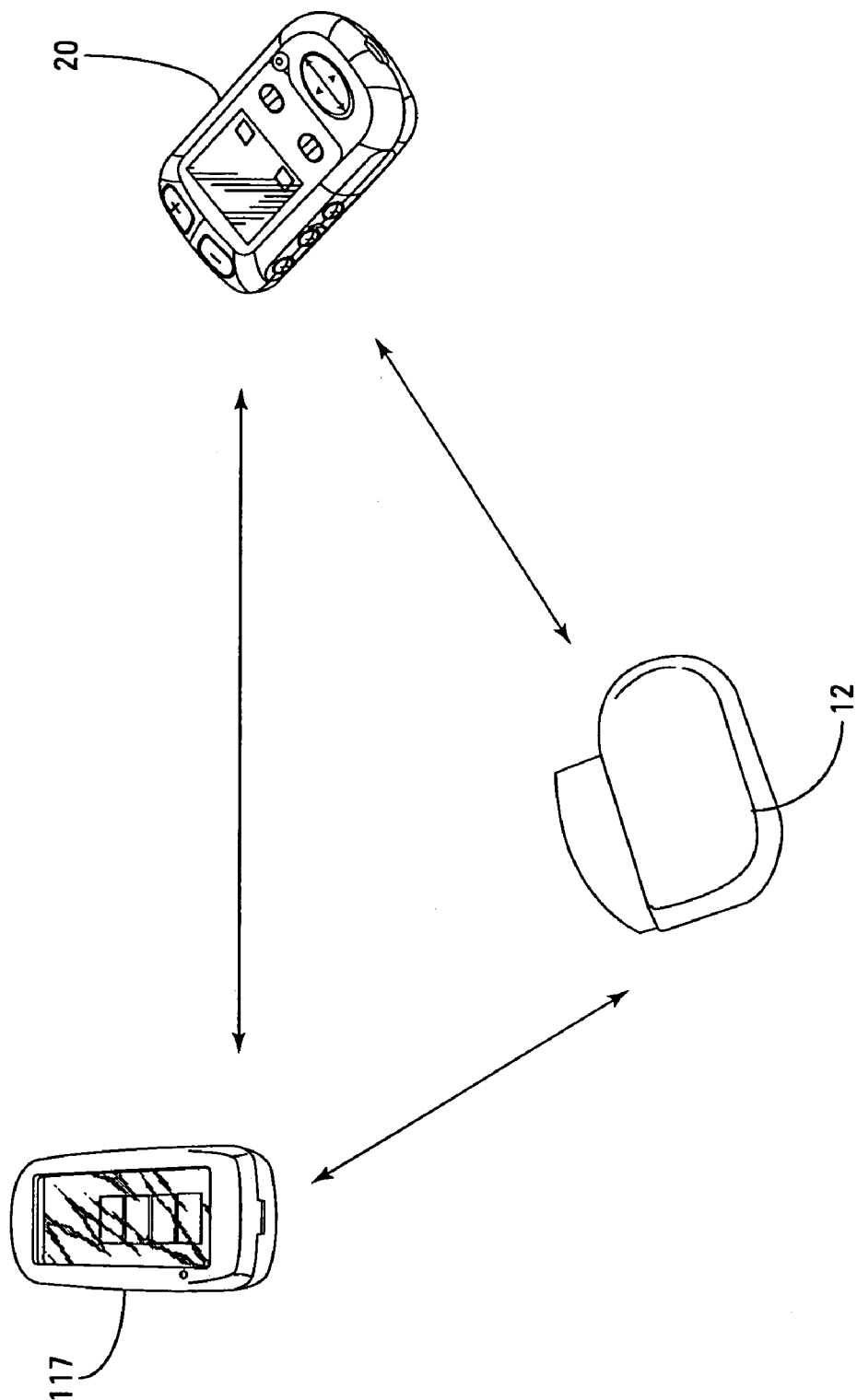
FIG. 22 is a perspective view of a medical device system including a clinician programmer, patient programmer and implantable medical device.

FIG. 22 is a perspective view illustrating a neurostimulation system including a clinician programmer 117, patient programmer 20 and LMD 12. The system includes IMD 12, which delivers neurostimulation therapy to patient 18 via one or more implanted leads. Clinician programmer 117 is used by a clinician to program neurostimulation therapy for patient 18. In particular, the clinician may use programmer 117 to create neurostimulation therapy programs. As part of the program creation process, programmer 117 allows the clinician to identify parameter settings and electrode configurations that enable IMD 12 to deliver neurostimulation therapy that is desirable in terms of, for example, symptom relief, coverage area relative to symptom area, and side effects.

Programmer 117 may also allow the clinician to identify parameter settings that enable IMD 12 to deliver effective neurostimulation therapy with desirable device performance characteristics, e.g., low battery consumption. Programmer 117 controls IMD 12 to test parameter settings in order to allow a clinician to identify desirable configurations in an efficient manner. Once clinician programmer 117 has loaded IMD 12 with neurostimulation therapy programs, the patient then uses patient programmer 20 to modify and select programs and parameter settings. Clinician programmer 117 may be configured to incorporate features described herein with respect to patient programmer 20. Accordingly, features attributed to patient programmer 20 may be applicable to the design of other programmers such as a clinician programmer, in accordance with the invention.

Figure 23:
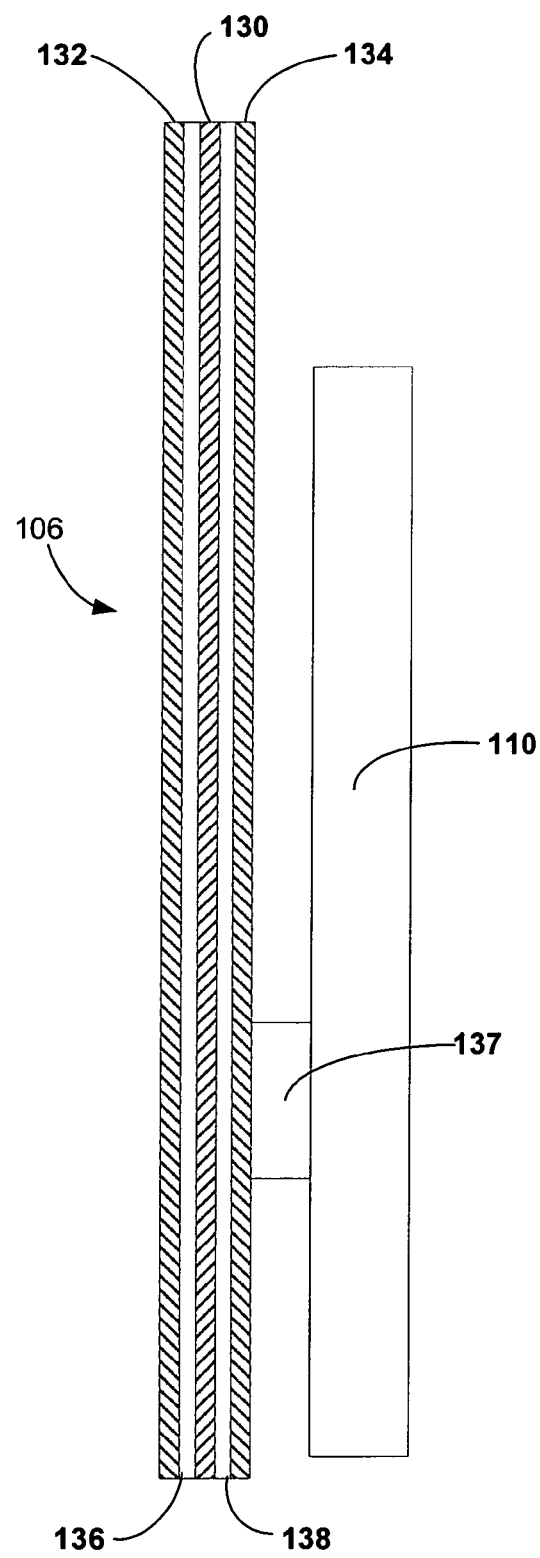
FIG. 23 is a conceptual side view of an antenna circuit board for use in a programmer.

FIG. 23 is a conceptual side view of an antenna circuit board 106 for use in a programmer 20. Antenna circuit board 106 is not necessarily in proportion, but provides an illustration of various layers of the circuit board, which is coupled to antenna 110 via a connector 137. Connector 137 couples antenna 110 to circuit board 106. As described herein, antenna 110 may have a loop-like configuration that defines an aperture that may accommodate a battery bay. Antenna circuit board 106 may include a ground plane 130, a signal plane 132, and a signal plane 134. Optionally, a power plane carrying operating power may be provided within circuit board 106 or distributed across signal planes 132, 134.

Dielectric layer 136 separates ground plane 130 and signal plane 132. Similarly, dielectric layer 138 separates ground plane 130 and signal plane 134. Antenna circuit board 106, like display circuit board 104, may be constructed from conventional laminated circuit board materials. Ground plane 130 and signal planes 132, 134 may be formed from conductive coatings or layers, and etched or printed to define desired circuit traces. Signal planes 132, 134 may support a variety of surface mount components.

In accordance with another embodiment of the invention, ground plane 130 and signal planes 132, 134 may be configured to further promote telemetry performance. For example, ground plane 130 and signal planes 132, 134 may be configured to balance two competing objectives. First, a single, contiguous ground plane area is desirable to provide a low impedance return path for electrical signals transmitted via traces on signal planes 132, 134. A single, substantially contiguous ground plane 130 serves to maximize RF signal integrity.

Second, it is desirable to present a minimal magnetic load to the magnetic circuit operating on antenna 110. Reduction or elimination of surface area of conductive signal planes 132, 134 within the antenna aperture serves to reduce the magnetic load to the magnetic circuit of antenna 110. In other words, forming signal planes 132, 134 that define apertures in alignment with the aperture of antenna 110 can substantially reduce the magnetic load. The ground plane and signal plane features described herein may be especially suitable for antenna circuit board 106, but may also be useful with display circuit board 104.

Providing a single, contiguous ground plane 130 with signal planes 132, 134 defining apertures that correspond to the antenna aperture results in losses in the magnetic field strength generated by the antenna 110, and magnetic signal integrity is maximized. The apertures defined by signal planes 130, 132 may be substantially continuous. Alternatively, a "cross-hatched" conductive pattern within the signal plane areas corresponding to the antenna aperture can present a controlled, reduce magnetic load to the antenna.

Figure 24:
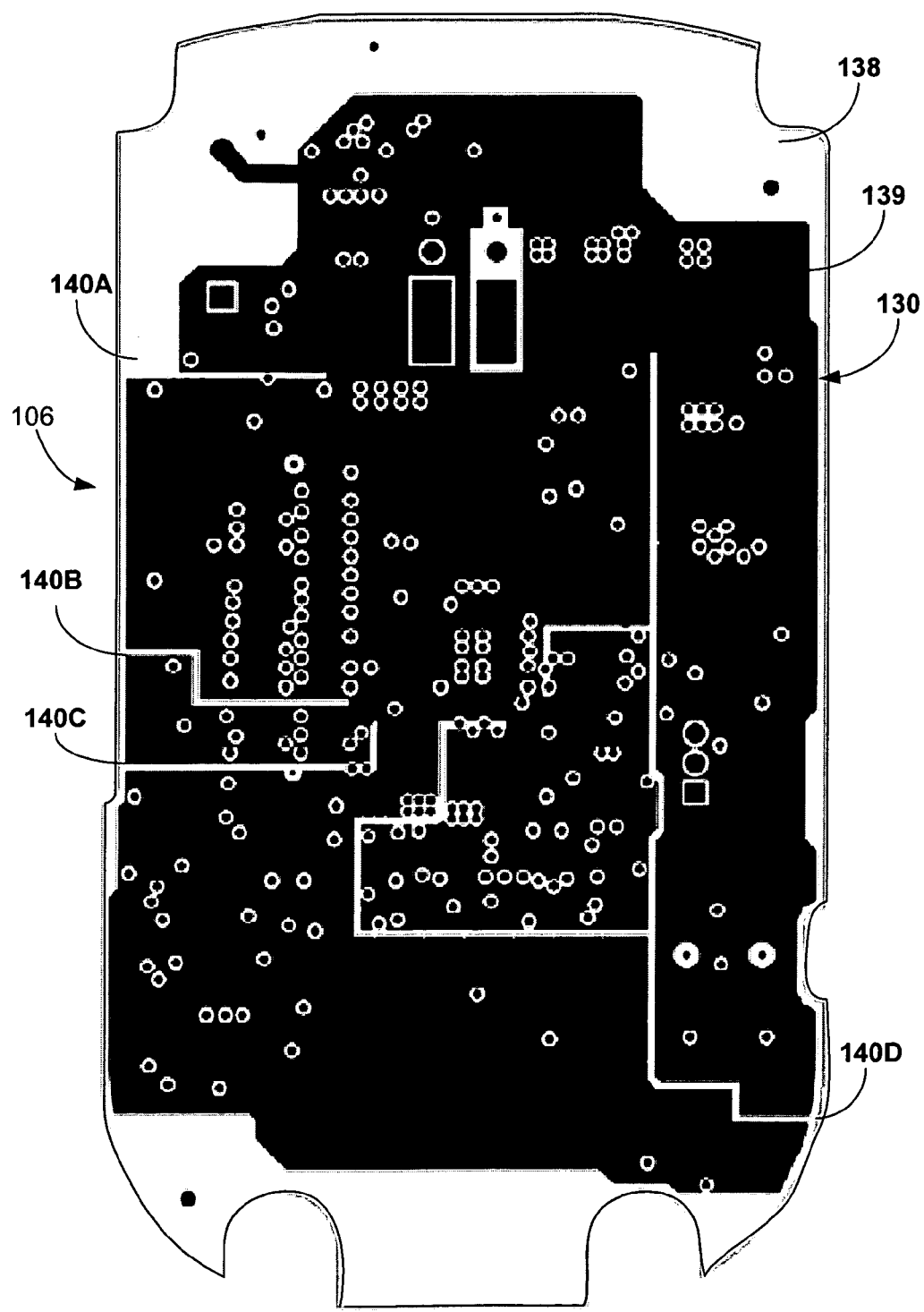
FIG. 24 is a plan view of a ground plane for an antenna circuit board as shown in FIG. 23.

FIG. 24 is a plan view of a ground plane 130 for an antenna circuit board 106 as shown in FIG. 23. As shown in FIG. 24, ground plane 130 extends over dielectric layer 138. In particular, ground plane 130 is formed by a conductive layer 139 that extends over a substantial area of dielectric layer 138 in a substantially contiguous manner. To achieve a working compromise between RF and magnetic requirements, the single, contiguous ground plane 130 is, in effect, divided into smaller plane areas primarily to minimize magnetic loading of the antenna.

The exact dimensions of each smaller plane area may not be critical to minimizing the loading. However, the desired effect of good RF and magnetic performance can be realized by incorporating a series of channel-like gaps 140A-140D (the various white lines in FIG. 24) that extend outward from an inner area of ground plane 130 toward outer edges of antenna circuit board 106. Not all of the gaps are associated with reference numerals due to limitation in the black-on-white presentation of FIG. 24. The width of each gap 140 may vary, but can be on the order of approximately 0.2 to 3.0 mm.

The spoke-like pattern of gaps may emanate from the center of antenna circuit board and extend outward toward the edges, interrupting the continuous ground plane and defining sub-areas. There is no conductive material in the gaps 140A-140D. These gaps 140A-140D divide adjacent conductive plane areas of ground plane 130 to prevent large eddy currents from forming around the perimeter of antenna circuit board 106 in the conductive plane because there are no conductive loops around the perimeter of the board.

The island-like plane areas defined by gaps 140A-140D may vary in size and shape, and need not be entirely decoupled from one another. Rather, the plane areas may be electrically coupled to another but separated to some extent by respective gaps 140A-140D. In some embodiments, the number of small plane areas defined by gaps 140A-140D may be determined according to the functional grouping of electrical signals carried in corresponding regions of signal planes 130, 132. In order to maintain signal integrity, for example, all digital signals may be grouped into one area; all analog signals may be grouped into a second area; and so forth. Each small area of ground plane 130 can provide sufficiently low impedance return paths to maintain signal integrity for the respective signal groups.

Figure 25:
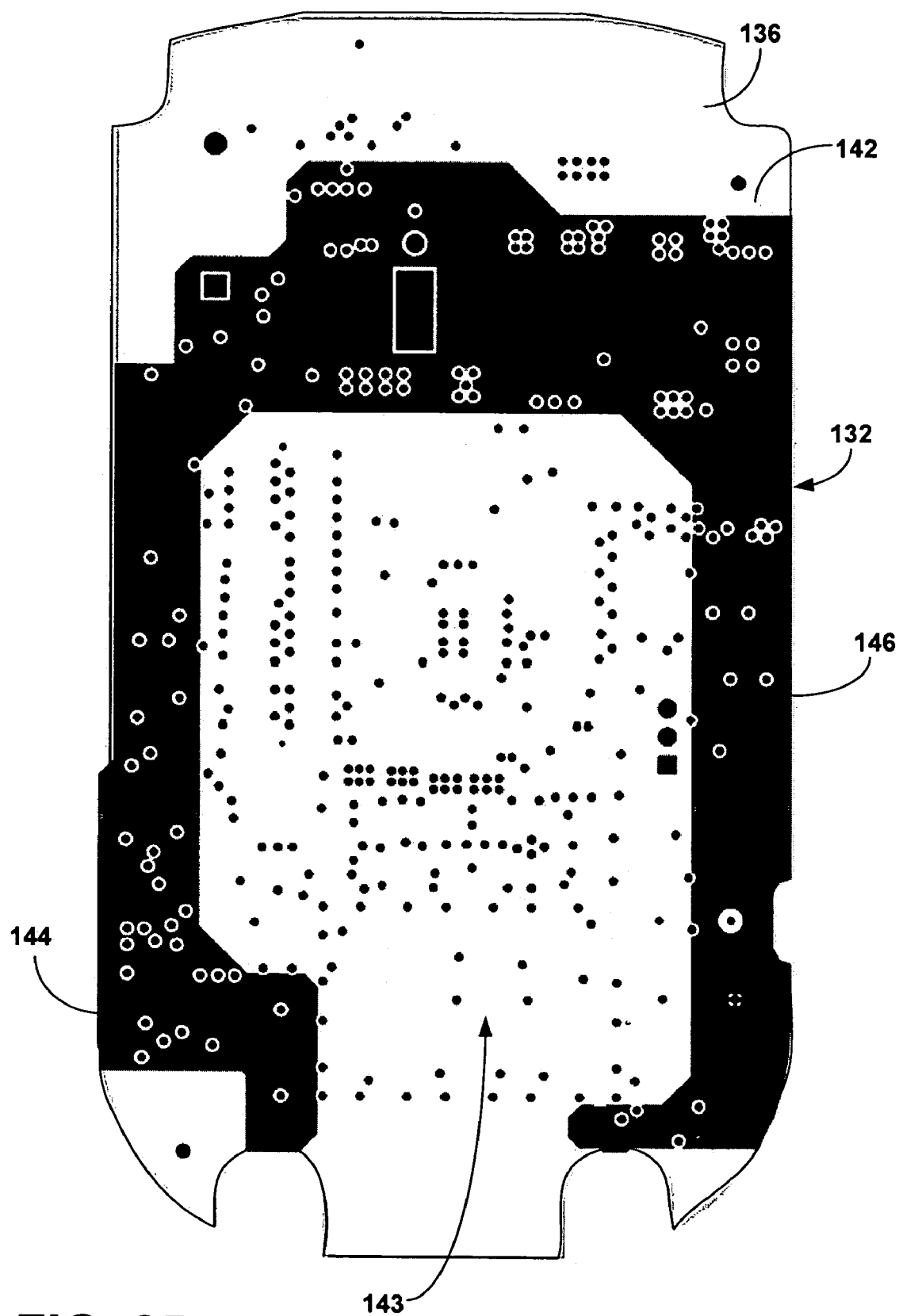
FIG. 25 is a plan view of a first signal plane for an antenna circuit board as shown in FIG. 23.
Figure 26:
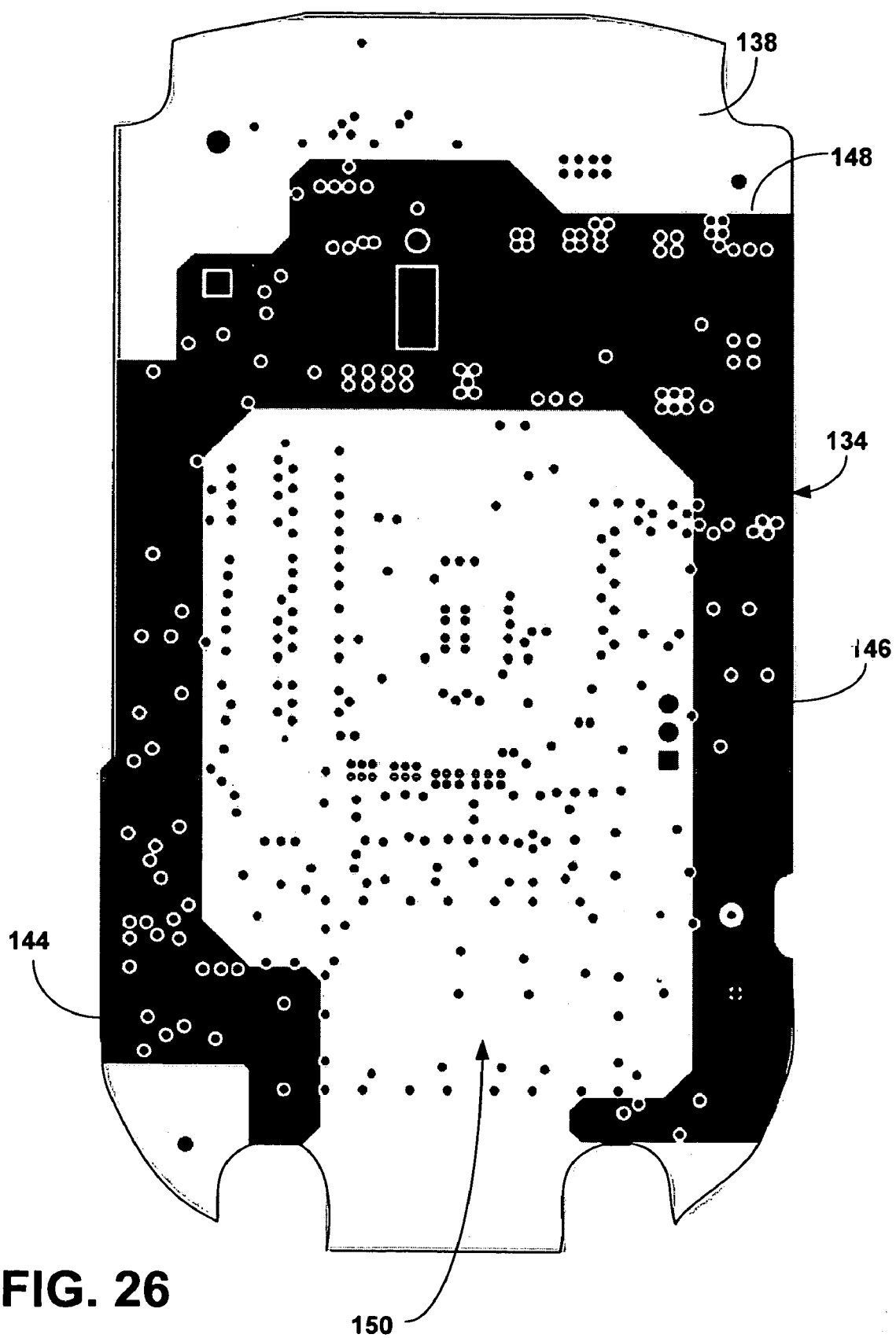
FIG. 26 is a plan view of a second signal plane for an antenna circuit board as shown in FIG. 23.

FIG. 25 is a plan view of a first signal plane 132 for an antenna circuit board 106 as shown in FIG. 23. FIG. 26 is a plan view of a second signal plane 134 for an antenna circuit board 106 as shown in FIG. 23. First signal plane 132 is shown in conjunction with dielectric layer 136, while second signal plane 134 is shown in conjunction with dielectric layer 138. In the example of FIGS. 25 and 26, the respective signal planes 132, 134 may include conductive, electrostatic discharge (ESD) layers 142, 148, respectively.

The respective layers 142, 148 define central apertures 143, 150 that substantially correspond in size and shape to the aperture of antenna 110, which is mounted over the signal planes. For example, the apertures 143, 150 may approximate the size and shape of the aperture of antenna 110, although not necessarily exactly, and are positioned in alignment with the antenna aperture. The shapes of ESD layers 142, 148 may be accomplished by deposition, printing, etching or other fabrication techniques.

Both layers 142, 148 are dedicated to ESD protection of the antenna circuit board 106 by deliberately bringing the copper out to the left and right edges 144, 146 of the board 106 and connecting them to the main ground of the board only at the top and middle sections of copper. With this configuration, any ESD events have a known and controlled conductive path to main ground, and the disruptive effects of ESD are minimized. In the example of FIG. 25, the top and bottom edges of the PCB are not as well protected from ESD as the left and right edges, but these areas are not flooded with copper to prevent magnetic loading effects, as described above.

Various embodiments of the invention have been described. However, one skilled in the art will appreciate that various additions and modifications can be made to these embodiments without departing from the scope of the invention. The invention may be generally applicable to any programmer useful with an implanted medical device, including patient programmers or physician programmers within the context of the clinical programming environment.

The implantable medical device may provide stimulation therapies for pain and movement disorders and may include other stimulation-based therapies as well. Also, programmer in accordance with the invention may be applicable to other implantable medical devices such as implantable drug delivery devices, and implantable cardiac pacemakers, cardioverters, or defibrillators, as well as non-implanted, external medical devices such as stimulators, drug pumps, or the like, and medical devices including both implanted and external components. These and other embodiments are within the scope of the following claims.

The invention claimed is:

1. A medical device programmer comprising a first housing member, a second housing member, a display, a plate member attached to the second housing member, a first circuit board, and a second circuit board substantially enclosed within the first housing member and the second housing member, wherein the plate member covers at least a portion of the display and includes a transparent area that exposes the display for viewing, and the plate member is printed with information to identify a programmer type associated with the medical device programmer, and wherein the first circuit board includes telemetry circuitry and the second circuit board includes the display and display circuitry and wherein the second housing member defines an aperture for access to a software loading port, the plate member being sized to cover the aperture upon placement of the plate member on the second housing member.

2. The programmer of claim 1, wherein the plate member is printed to include personalization information to identify a patient.

3. The programmer of claim 1, wherein the plate member is printed to include personalization information to identify a clinic.

4. The programmer of claim 1, wherein the plate member is printed with graphic information.

5. The programmer of claim 1, wherein the plate member is printed with text information.

6. The programmer of claim 1, wherein the plate member is molded to define one or more apertures to accommodate buttons extending outward from the programmer.

7. A programmer comprising a first housing member, a second housing member, a display, and a plate member attached to the second housing member, wherein the plate member covers at least a portion of the display and includes a transparent area that exposes the display for viewing, and the plate member is printed with information to identify a programmer type associated with the medical device programmer, and wherein the second housing member defines an aperture for access to a software loading port, the plate member being sized to cover the aperture upon placement of the plate member on the second housing member.

8. The programmer of claim 7, wherein the software loading port is a JTAG port.

9. The programmer of claim 1, wherein the plate member is selected from one of a plurality of plate members having different configurations based on a match between the configuration of the plate member and a type of medical device programmer being assembled.

10. The programmer of claim 9, wherein the plate member configuration comprises a size, a shape, a printed graphic, and a number of apertures to accommodate input buttons extending outward from the programmer.

11. The programmer of claim 1, further comprising an infrared interface to receive changes to software executed by a processor within the programmer during an infrared communication session.

12. The programmer of claim 1, further comprising power control circuitry to reduce input voltage to a predetermined level to minimize noise levels within the programmer.

13. The programmer of claim 1, wherein the display is a liquid crystal display.

14. The programmer of claim 1, wherein the second circuit board includes control circuitry to drive the telemetry circuitry and the display circuitry.

15. The programmer of claim 1, wherein the first circuit board includes an internal antenna.

16. The programmer of claim 7, wherein the plate member is printed to include personalization information to identify a patient.

17. The programmer of claim 7, wherein the plate member is printed to include personalization information to identify a clinic.

18. The programmer of claim 7, wherein the plate member is printed with graphic information.

19. The programmer of claim 7, wherein the plate member is printed with text information.

20. The programmer of claim 7, wherein the plate member is molded to define one or more apertures to accommodate buttons extending outward from the programmer.

21. The programmer of claim 7, wherein the plate member is selected from one of a plurality of plate members having different configurations based on a match between the configuration of the plate member and a type of medical device programmer being assembled.

22. The programmer of claim 21, wherein the plate member configuration comprises a size, a shape, a printed graphic, and a number of apertures to accommodate input buttons extending outward from the programmer.

23. The programmer of claim 7, further comprising an infrared interface to receive changes to software executed by a processor within the programmer during an infrared communication session.

24. The programmer of claim 7, further comprising power control circuitry to reduce input voltage to a predetermined level to minimize noise levels within the programmer.

25. The programmer of claim 7, wherein the display is a liquid crystal display.

26. The programmer of claim 7, further comprising a first circuit board and a second circuit board substantially enclosed within the first housing member and the second housing member.

27. The programmer of claim 26, wherein the first circuit board includes telemetry circuitry and the second circuit board includes the display and display circuitry.

28. The programmer of claim 27, wherein the second circuit board includes control circuitry to drive the telemetry circuitry and the display circuitry.

29. The programmer of claim 27, wherein the first circuit board includes an internal antenna.

30. The programmer of claim 1, wherein the second housing member defines an aperture for access to a software loading port, the plate member being sized to cover the aperture upon placement of the plate member on the second housing member.

31. The programmer of claim 30, wherein the software loading port is a JTAG port.

* * * * *